US012622793B2

(12) United States Patent
Ide et al.

(10) Patent No.: US 12,622,793 B2
(45) Date of Patent: May 12, 2026

(54) SYNTHETIC RESIN STENT AND STENT DELIVERY SYSTEM

(71) Applicant: JMS CO., LTD., Hiroshima (JP)

(72) Inventors: Junichi Ide, Hiroshima (JP); Shuji Fukutaki, Hiroshima (JP); Manami Nishihara, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 1262 days.

(21) Appl. No.: 17/599,417

(22) PCT Filed: Mar. 30, 2020

(86) PCT No.: PCT/JP2020/014487
§ 371 (c)(1),
(2) Date: Sep. 28, 2021

(87) PCT Pub. No.: WO2020/196912
PCT Pub. Date: Oct. 1, 2020

(65) Prior Publication Data
US 2022/0211524 A1     Jul. 7, 2022

(30) Foreign Application Priority Data

Mar. 28, 2019    (JP) ................................. 2019-063124

(51) Int. Cl.
*A61F 2/852*       (2013.01)
*A61F 2/00*        (2006.01)
*A61F 2/90*        (2013.01)

(52) U.S. Cl.
CPC ................ *A61F 2/852* (2013.01); *A61F 2/90* (2013.01); *A61F 2002/0081* (2013.01);
(Continued)

(58) Field of Classification Search
CPC .... A61F 2/852; A61F 2/90; A61F 2/82; A61F 2/89; A61F 2002/91558; A61F 2002/821; A61F 2002/826; A61F 2002/91591
See application file for complete search history.

(56) References Cited

U.S. PATENT DOCUMENTS 5,843,167 A      12/1998  Dwyer
6,221,100 B1 *    4/2001  Strecker .................... A61F 2/90
                                                        623/1.22
(Continued)

FOREIGN PATENT DOCUMENTS

EP          1645246 A1 *   4/2006   ............... A61F 2/90
EP          3245984 A1    11/2017
(Continued)

OTHER PUBLICATIONS

Translation of EP1645246A1 (Year: 2006).*
Translation of EP1645246 (Year: 2006).*

*Primary Examiner* — Christie Bahena
(74) *Attorney, Agent, or Firm* — MUNCY, GEISSLER, OLDS & LOWE, P.C.

(57)                    ABSTRACT

A synthetic resin stent is able to demonstrate self-extensibility, restorability, adhesion to the digestive tract, and ability to follow peristaltic movement. The synthetic resin stent is provided with: a first stent that has a first stent body formed as a cylindrical mesh from fibers made of synthetic resin, and that can be deformed from a reduced-diameter state to an expanded-diameter state; and a second stent that is formed as a cylindrical mesh which is finer than that of the first stent body, is arranged so as to cover the outer periphery of the first stent body, and can be deformed from a reduced-diameter state to an expanded-diameter state.

17 Claims, 15 Drawing Sheets

(52) U.S. Cl.
CPC . *A61F 2250/001* (2013.01); *A61F 2250/0026*
(2013.01); *A61F 2250/0039* (2013.01)

(56)     References Cited

U.S. PATENT DOCUMENTS

| | | | |
|---|---|---|---|
| 6,241,757 B1 | 6/2001 | An | |
| 2007/0191922 A1 | 8/2007 | Hartley | |
| 2008/0262628 A1 * | 10/2008 | Laitenberger | A61F 2/915 |
| | | | 623/23.7 |
| 2010/0249902 A1 | 9/2010 | Sakai | |
| 2010/0318171 A1 | 12/2010 | Porter | |
| 2013/0131780 A1 | 5/2013 | Armstrong et al. | |
| 2013/0226282 A1 | 8/2013 | Ahn | |

FOREIGN PATENT DOCUMENTS

| | | | | |
|---|---|---|---|---|
| JP | 8-299456 A | 11/1996 | | |
| JP | 10-272190 A | 10/1998 | | |
| JP | 2003052834 A | 2/2003 | | |
| JP | 2005211292 A | 8/2005 | | |
| JP | 2008200293 A | 9/2008 | | |
| JP | 2017169990 A | 9/2017 | | |
| KR | 10-20180003877 A | 1/2018 | | |
| WO | WO-0135864 A1 * | 5/2001 | | A61F 2/90 |
| WO | WO2020196913 A1 | 10/2020 | | |

* cited by examiner

(a) Case in which a biodegradable stent is placed in the intestinal tract of φ 16 mm (fiber: using No. 0 fiber (about φ 0.4 mm))

Tip angle θ [°] of the end flare portion; one side length L (mm) (theoretical value)

| Number of peaks \ Pitch P1[mm] | 7.0 | 8.7 | 11.0 | 11.8 | 13.5 | 16.3 | 19.0 | 22.0 |
|---|---|---|---|---|---|---|---|---|
| 3 — Tip angle (°) | 111.6 | 97.4 | 83.1 | 78.4 | 70.7 | 60.5 | 52.8 | 46.4 |
| 3 — One side length L (mm) | 10.9 | 12.1 | 13.8 | 14.5 | 15.9 | 18.3 | 20.8 | 23.5 |

| Number of peaks \ Pitch P1[mm] | 5.6 | 7.7 | 10.1 | 11.0 | 12.8 | 15.7 | 18.7 | 21.5 |
|---|---|---|---|---|---|---|---|---|
| 4 — Tip angle (°) | 107.6 | 87.5 | 70.8 | 65.9 | 57.9 | 48.5 | 41.5 | 36.2 |
| 4 — One side length L (mm) | 8.4 | 9.9 | 11.9 | 12.7 | 14.3 | 16.9 | 19.6 | 22.4 |

(b) Case in which a biodegradable stent is attached to a core rod of φ 20 mm (fiber: using No. 0 fiber (about φ 0.4mm))

Tip angle θ [°] of the end flare portion; one side length L (mm) (theoretical value)

| Number of peaks \ Pitch P1[mm] | 3.0 | 6.0 | 9.0 | 10.0 | 12.0 | 15.0 | 18.0 | 21.0 |
|---|---|---|---|---|---|---|---|---|
| 3 — Tip angle (°) | 164.5 | 133.8 | 109.6 | 102.9 | 91.4 | 77.6 | 67.1 | 58.9 |
| 3 — One side length L (mm) | 10.9 | 12.1 | 13.8 | 14.5 | 15.9 | 18.3 | 20.8 | 23.5 |
| 4 — Tip angle (°) | 153.5 | 116.9 | 91.4 | 84.8 | 73.8 | 61.4 | 52.4 | 45.6 |
| 4 — One side length L (mm) | 8.4 | 9.9 | 11.9 | 12.7 | 14.3 | 16.9 | 19.6 | 22.4 |

FIG. 7

Evaluation result 1

Fiber: No. 0 (about φ 0.4 mm)   ▨ Range in which the distance in migration was 1 cm or less after repeating peristaltic movement 10 times (including estimation)

(a) Number of the peaks 721 of the end flare portion 72 is three

| | | | | | Tip angle (°) | | | | | |
|---|---|---|---|---|---|---|---|---|---|---|
| One side length L (mm) | 46.4 | 52.8 | 58.9 | 60.5 | 67.1 | 70.7 | 77.6 | 78.4 | 91.4 | 102.9 |
| 14.5 | | | | | | | | | | |
| 15.9 | | | | | | | | | | 2.4 |
| 16.9 | | | | | | | | | 1.3 | |
| 18.3 | | | | | | 0.9 | 0.3 | 0.9 | | |
| 20.8 | | 0.3 | | 0.1 | 0.2 | | | | | |
| 23.5 | 0.2 | | 0.3 | | | | | | | |

Fiber: No. 0 (about φ 0.4 mm)   ▨ Range in which the distance in migration was 1 cm or less after repeating peristaltic movement 10 times (including estimation)

(b) Number of the peaks 721 of the end flare portion 72 is four

| | | | | | | Tip angle θ (°) | | | | | | |
|---|---|---|---|---|---|---|---|---|---|---|---|---|
| One side length L (mm) | 36.2 | 41.5 | 45.6 | 48.5 | 52.4 | 57.9 | 61.4 | 65.9 | 70.8 | 73.8 | 84.8 | 87.5 |
| 9.9 | | | | | | | | | | | | |
| 11.9 | | | | | | | | | | | | 5.7 |
| 12.7 | | | | | | | | 1.2 | 1.9 | | 3.9 | |
| 14.3 | | | | | | 1.1 | | | | 2.3 | | |
| 16.9 | | | | 0.4 | | | 0.7 | | | | | |
| 19.6 | | 0.2 | | | 0.2 | | | | | | | |
| 22.4 | 0.2 | | 0.3 | | | | | | | | | |

Evaluation result 2

FIG. 8

Fiber No. 1 (about φ 0.5 mm)   ▒ Range in which the distance in migration was 1 cm or less after repeating peristaltic movement 10 times (including estimation)

(a) Number of the peaks 721 of the end flare portion 72 is three

| | | Tip angle θ (°) | | | | | | | | | |
|---|---|---|---|---|---|---|---|---|---|---|---|
| | | 46.4 | 52.8 | 58.9 | 60.5 | 67.1 | 70.7 | 77.6 | 78.4 | 91.4 | 102.9 |
| One side length L (mm) | 14.5 | | | | | | | | | | |
| | 15.9 | | | | | | 1.9 | | 0.5 | 3.3 | 2.6 |
| | 18.3 | | | | 0.7 | | | 2.2 | | | |
| | 20.8 | | 0.3 | | | 0.9 | | | | | |
| | 23.5 | 0.0 | | 0.7 | | | | | | | |

Fiber No. 1 (about φ 0.5 mm)   ▒ Range in which the distance in migration was 1 cm or less after repeating peristaltic movement 10 times (including estimation)

(b) Number of the peaks 721 of the end flare portion 72 is four

| | | Tip angle θ (°) | | | | | | | | | |
|---|---|---|---|---|---|---|---|---|---|---|---|
| | | 36.2 | 41.5 | 45.6 | 48.5 | 52.4 | 57.9 | 61.4 | 65.9 | 73.8 | 84.8 |
| One side length L (mm) | 12.7 | | | | | | | | | | |
| | 14.3 | | | | | | 0.1 | | 0.3 | 2.5 | 3.8 |
| | 16.9 | | | | 0.1 | | | 0.7 | | | |
| | 19.6 | | 0.1 | | | 0.3 | | | | | |
| | 22.4 | 0.2 | | 0.2 | | | | | | | |

SYNTHETIC RESIN STENT AND STENT DELIVERY SYSTEM

TECHNICAL FIELD

The present invention relates to a synthetic resin stent such as a biodegradable stent, and to a stent delivery system.

BACKGROUND ART

Stenotic diseases (such as tumors and inflammations) in natural tracts such as blood vessels and gastrointestinal tracts are heretofore treated by placing a stent at a stenotic site and dilating the stenotic site. Stents made of metal or synthetic resin are known, for example. Among these, when a metal stent is removed from the body, a surgical intervention is needed and imposes a significant burden on the patient. Therefore, use of a metal stent is limited to cases such as malignant tumors for which semi-permanent placement or surgical procedures are planned. Against such a background, a biodegradable stent as a synthetic resin stent has been proposed as a stent for use in cases where a metal stent cannot be used.

A synthetic resin stent is inferior to a metal stent, in self-expandability, restorability, adherence to the gastrointestinal tract such as the intestinal tract, and trackability to peristaltic movement of the gastrointestinal tract; therefore, required performance may not be achieved when a synthetic resin stent is manufactured in the same shape as a metal stent. On the other hand, for example, a stent formed by connecting biodegradable resin processed into a zigzag shape and covered with a membrane is disclosed (e.g., see Patent Document 1).

Patent Document 1: Japanese Unexamined Patent Application, Publication No. 2003-52834

DISCLOSURE OF THE INVENTION

Problems to be Solved by the Invention

However, since the stent disclosed in Patent Document 1 is covered with a membrane, it is difficult to reduce the diameter of the stent. Since the stent disclosed in Patent Document 1 is formed by connecting biodegradable resin processed into a zigzag shape, it is difficult to balance the functions of the stent, the ends of which essentially require trackability or restorability in relation to peristaltic movement of the gastrointestinal tract, and the central portion of which requires pressure strength. Therefore, a synthetic resin stent capable of achieving self-expandability, restorability, adherence to the gastrointestinal tract, and trackability to peristaltic movement of the gastrointestinal tract has been desired.

Accordingly, it is an object of the present invention to provide a synthetic resin stent and a stent delivery system capable of achieving self-expandability, restorability, adherence to the gastrointestinal tract, and trackability to peristaltic movement of the gastrointestinal tract.

Means for Solving the Problems

The present invention relates to a synthetic resin stent, including: a first stent including a first stent body formed of synthetic resin fiber into a tubular structure having a mesh, the first stent being deformable from a reduced diameter state to an expanded diameter state; and a second stent formed into a tubular structure having a mesh denser than the mesh of the first stent body, the second stent arranged so as to cover an outer periphery of the first stent body, and being deformable from the reduced diameter state to the expanded diameter state.

The first stent body is preferably formed by connecting a plurality of polygonal annular portions side by side in a longitudinal direction of the first stent, in a state in which the polygonal annular portions formed of synthetic resin fiber into a polygonal annular shape as viewed in the longitudinal direction are bent or curved so as to be convex in the longitudinal direction.

The first stent preferably further includes an end enlarged diameter portion connected to at least one end of the first stent body in the longitudinal direction, the end enlarged diameter portion being larger in diameter than the first stent body.

The first stent body is preferably connected side by side to the first stent in the longitudinal direction, in a state in which the plurality of polygonal annular portions formed of synthetic resin fiber into a polygonal annular shape as viewed in the longitudinal direction are bent or curved so as to be convex in the longitudinal direction; and the end enlarged diameter portion formed of synthetic resin fiber having a diameter smaller than that of the first stent body is preferably configured into a polygonal annular structure being more polygonal than the polygonal annular portions.

The first stent is preferably a stent including an end flare portion arranged at an end in an axial direction, the first stent being formed of wires; a plurality of peaks composed of tip corners protruding outward in the axial direction are preferably consecutively arranged in a circumferential direction, whereby the end flare portion is formed into an annular shape as viewed in the axial direction; an angle formed by two sides of each of the peaks is preferably 80° or less in a state in which the stent is placed inside the gastrointestinal tract; and the number of the plurality of peaks is preferably three to eleven.

The two sides composing each of the peaks are preferably composed of two sides of an end grid arranged at an end in the axial direction.

The first stent preferably includes a plurality of grids arranged side by side in the axial direction; and the end grid is preferably arranged at an end of the plurality of grids.

One side length of one of the two sides composing each of the peaks is preferably 16 mm to 22 mm.

Adjacent ones of the peaks of the end flare portion are preferably fixed at an intersection to the most end-side in the axial direction.

The second stent is preferably a synthetic resin stent including a first woven component portion being tubular and composed of a plurality of fibers woven into a mesh, and a second woven component portion composed of a plurality of fibers arranged so as to be woven into the first woven component portion and configured into an annular shape; the first woven component portion preferably includes a plurality of first fibers extending so as to be inclined at a predetermined angle with respect to the axial direction, a plurality of second fibers extending so as to intersect with the first fibers, and a plurality of first intersecting points configured with intersections of the plurality of first fibers and the plurality of second fibers; the second woven component portion preferably includes a plurality of wave-shaped third fibers arranged so as to be spaced apart in the axial direction, and a plurality of wave-shaped fourth fibers arranged so as to be spaced apart in the axial direction; and at least one first intersecting point of the plurality of first intersecting points is preferably arranged in intersecting regions surrounded by the third fibers and the fourth fibers.

The plurality of intersecting regions are preferably formed side by side in the circumferential direction of the first woven component portion; and the plurality of first intersecting points are preferably arranged side by side in the circumferential direction of the first woven component portion and arranged in the plurality of intersecting regions, respectively.

In a configuration in which the first intersecting points are arranged in the intersecting regions, respectively, the third fibers are preferably arranged in a state of being hookable by one or more of the first fibers, the second fibers and the fourth fibers, in relation to movement in a direction in which an overlapping portion of the third fibers and the fourth fibers shrinks in size; and the fourth fibers is preferably arranged in a state of being hookable by one or more of the first fibers, the second fibers and the third fibers, in relation to movement in a direction in which the overlapping portion of the third fibers and the fourth fibers shrinks in size.

A plurality of configurations are provided in which the first intersecting point is arranged in the intersecting region, in which the synthetic resin stent is preferably configured to partly include a configuration, in which the third fibers and the fourth fibers are arranged in a state of being mutually hookable, in relation to movement in a direction in which the overlapping portion of the third fibers and the fourth fibers shrinks in size, and arranged in a state of not being hookable by the first fibers and the second fibers when the third fibers and the fourth fibers move.

A loop having a loop shape is preferably formed at the top of the peaks of the wave-shaped third fibers and/or the wave-shaped fourth fibers, the loop arranged so as to surround any one or more of the first fibers, the second fibers, the third fibers and the fourth fibers.

The second woven component portion is preferably formed of synthetic resin fiber having an expansion force higher than the first woven component portion.

The second stent is preferably a synthetic resin stent, including a first woven component portion being tubular and composed of one more fibers configured into a mesh, and a second woven component portion arranged so as to be woven into the first woven component portion and composed of one or more fibers configured into an annular shape; the first woven component portion preferably includes a plurality of first fibers repeatedly bent so as to be inclined at a predetermined angle with respect to the axial direction and extending in the axial direction, a plurality of second fibers arranged to include a portion intersecting with the first fibers and repeatedly bent so as to be inclined at a predetermined angle with respect to the axial direction and extending in the axial direction, and a plurality of first intersecting regions configured with intersections of the plurality of first fibers and the plurality of second fibers; the second woven component portion preferably includes a plurality of third fibers repeatedly bent so as to be inclined at a predetermined angle with respect to the axial direction and extending in the circumferential direction, a plurality of fourth fibers arranged to include a portion intersecting with the third fibers and repeatedly bent so as to be inclined at a predetermined angle with respect to the axial direction and extending in the axial direction, and a plurality of second intersecting regions configured with intersections of the plurality of third fibers and the plurality of fourth fibers; and the first intersecting regions and the second intersecting regions are preferably arranged to at least partly overlap with each other.

In a configuration in which the first intersecting region is arranged to overlap with the second intersecting region, the first fibers are preferably arranged in a state of being hookable by one or more of the third fibers and the fourth fibers, in relation to movement in a direction in which an overlapping portion of the first fibers and the second fibers shrinks in size; and the second fibers are preferably arranged in a state of being hookable by one or more of the third fibers and the fourth fibers, in relation to movement in a direction in which an overlapping portion of the first fibers and the second fibers shrinks in size.

The present invention further relates to a stent delivery system for placing the synthetic resin stent in vivo, the system including: an outer tube that can interiorly load the first stent and the second stent, in which the second stent and the first stent are arranged side by side in this order from the distal end side; and a pushing member that is arranged inside the outer tube and can extrude the second stent and the first stent in this order from the distal end side of the outer tube.

Effects of the Invention

The present invention can provide a synthetic resin stent and a stent delivery system having self-expandability, restorability, adherence to the gastrointestinal tract, and trackability to peristaltic movement of the gastrointestinal tract.

BRIEF DESCRIPTION OF THE DRAWINGS

FIG. 2 is a perspective view illustrating an inner stent of the first embodiment;

FIG. 6 is a table illustrating values of tip angles and one side lengths corresponding to the pitch and number of peaks of an end flare portion of a stent manufactured using fiber having a fiber diameter of φ 0.4 mm in relation to the inner stent of the second embodiment, in which (a) is a table illustrating values in a placed state, and (b) is a table illustrating values in a state attached to a core rod;

FIG. 7 is a table illustrating migration of the inner stent of the second embodiment in relation to peristaltic movement, in a case in which the biodegradable stent is placed inside the intestinal tract, in a case in which the tip angle and the one side length are changed in the end flare portion of the stent using fiber having a fiber diameter of φ 0.4 mm;

FIG. 8 is a table illustrating migration of the inner stent of the second embodiment in relation to peristaltic movement, in a case in which the biodegradable stent is placed inside the intestinal tract, in a case in which the tip angle and the one side length are changed in the end flare portion of the stent using fiber having a fiber diameter of φ 0.5 mm;

PREFERRED MODE FOR CARRYING OUT THE INVENTION

First Embodiment

Figure 1:
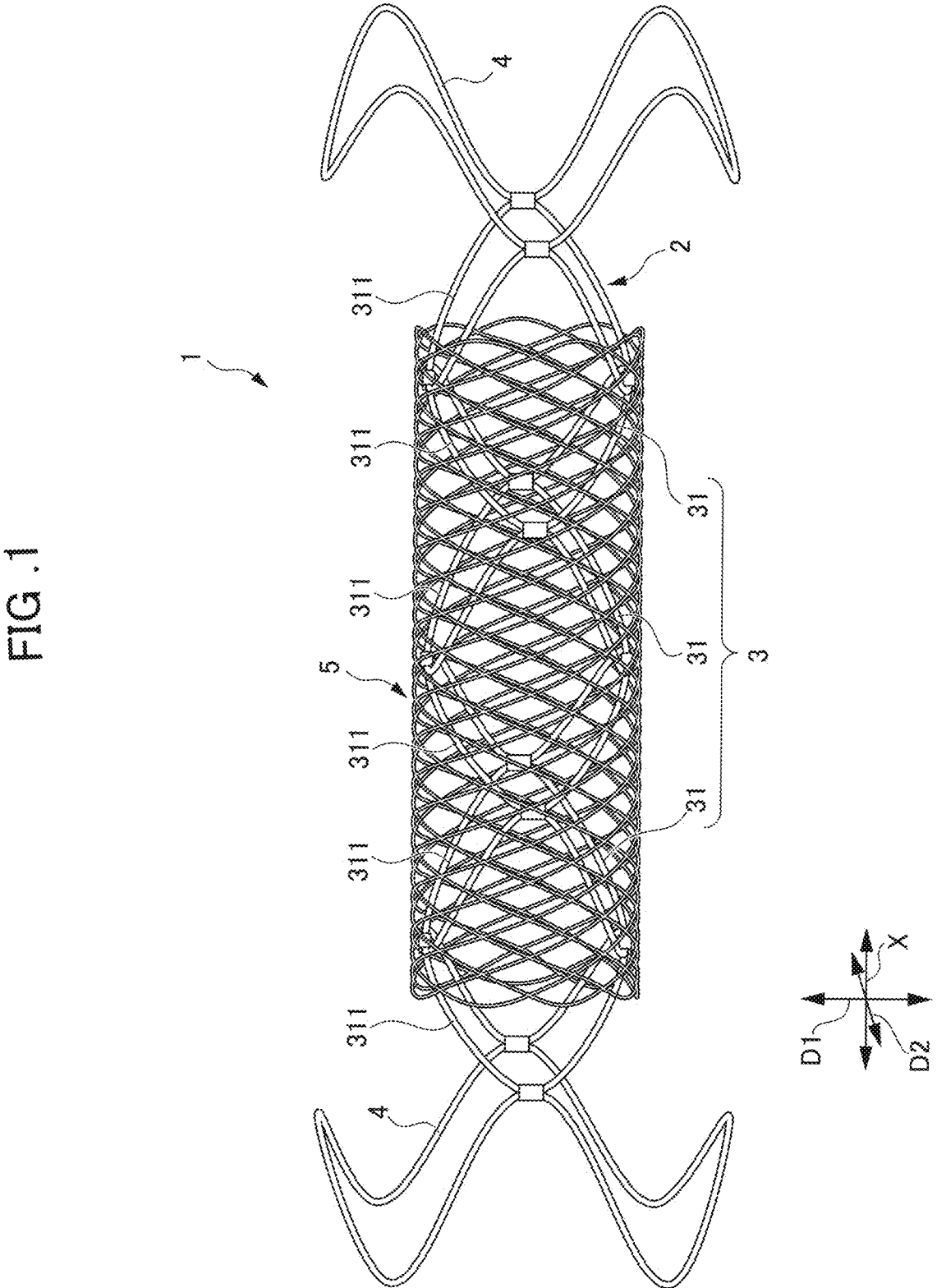
FIG. 1 is a perspective view illustrating a biodegradable stent according to a first embodiment of the present invention.
Figure 2:
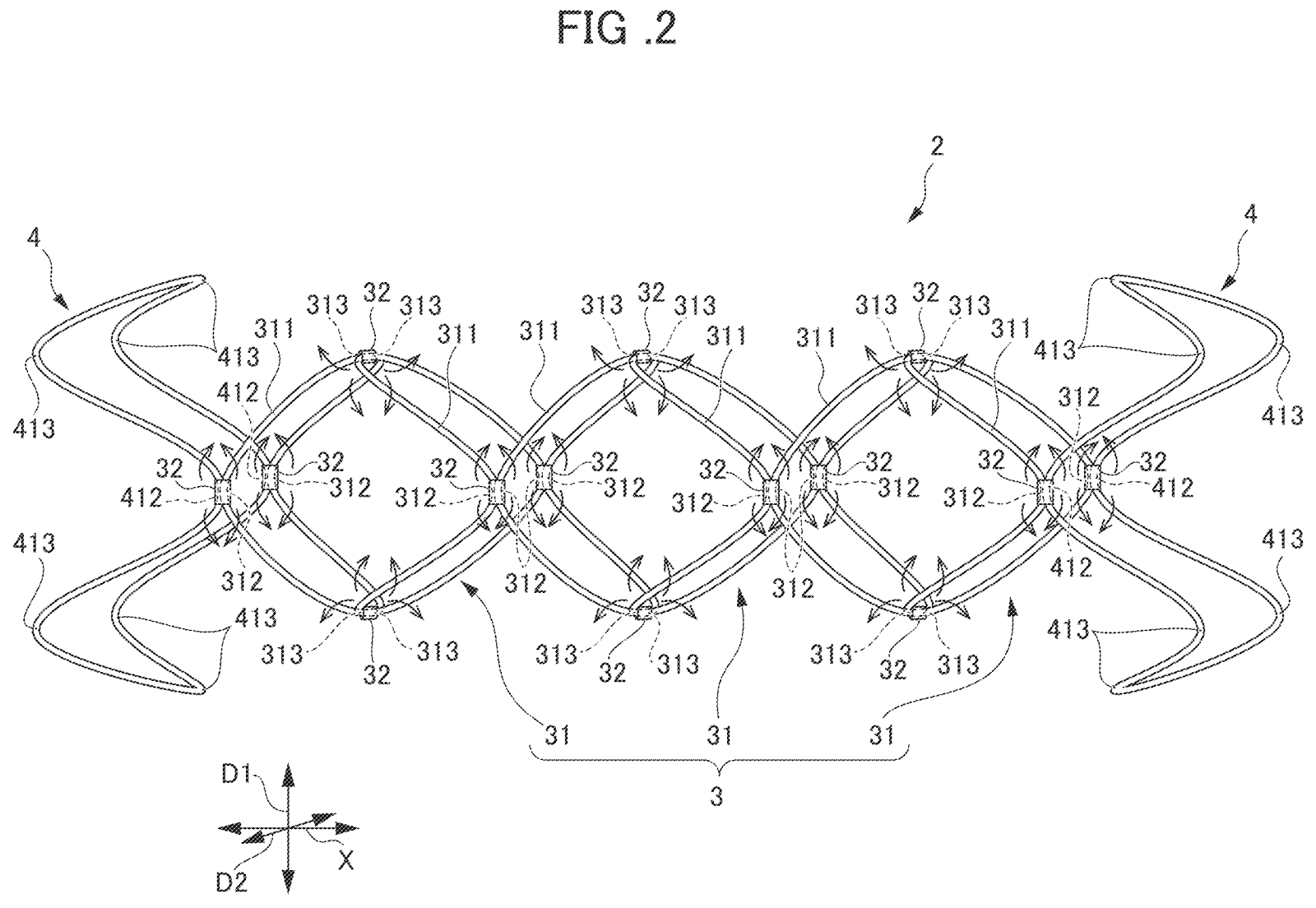
Figure 3:
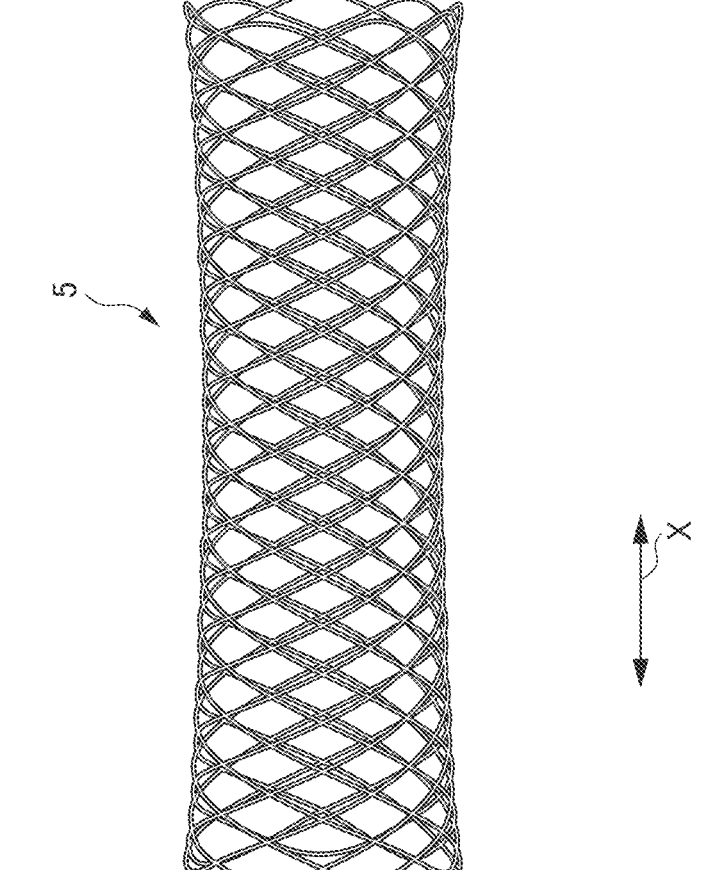
FIG. 3 is a perspective view illustrating an outer stent of the first embodiment.

Hereinafter, a first preferred embodiment of a synthetic resin stent of the present invention will be described with reference to the drawings. FIG. 1 is a perspective view illustrating a biodegradable stent 1 according to the first embodiment of the present invention. FIG. 2 is a perspective view illustrating an inner stent 2 of the first embodiment. FIG. 3 is a perspective view illustrating an outer stent 5 of the first embodiment. In the present embodiment, a direction in which the biodegradable stent 1 extends in its entirety is referred to as a longitudinal direction X; a direction orthogonal to the longitudinal direction X is referred to a first direction D1 which is the vertical direction in FIG. 1; and a direction orthogonal to both of the longitudinal direction X and the first direction D1 is referred to as a second direction D2.

The synthetic resin stent of the present embodiment is the biodegradable stent 1 composed of biodegradable fiber, and includes the inner stent 2 (first stent) and the outer stent 5 (second stent) being tubular as illustrated in FIGS. 1 to 3. The central part of the inner stent 2 in the longitudinal direction X is arranged inside the outer stent 5.

The inner stent 2 extends in the longitudinal direction X and is deformable from a reduced diameter state to an expanded diameter state. The inner stent 2 includes an inner stent body 3 (first stent body) formed as extending in the longitudinal direction X in its entirety, and a pair of end flare portions 4 (end enlarged diameter portions).

As illustrated in FIG. 2, the inner stent body 3 is formed of synthetic resin fiber into a tubular structure having a mesh, configuring a plurality of polygonal annular portions 311. The inner stent body 3 is configured by connecting the plurality of polygonal annular portions 311. More specifically, the inner stent body 3 is configured by connecting a plurality of three-dimensional portions 31 each configured by the pair of polygonal annular portions 311.

As illustrated in FIG. 2, the three-dimensional portion 31 is formed by connecting the pair of polygonal annular portions 311 in the longitudinal direction X. The polygonal annular portion 311 is formed by bending the annularly formed annular portion at a pair of bent portions 312 in the middle of the first direction D1 and at a pair of bent portions 313 in the middle of the second direction D2. The bent portions 312 and 313 are configured with peaks and valleys of the polygonal annular portion 311.

The polygonal annular portion 311 is formed into a square shape as viewed in the longitudinal direction X, or a substantially diamond shape in the present embodiment, for example. Both of the pair of bent portions 312 and the pair of bent portions 313 configuring the top of the polygonal annular portion 311 are bent into a substantially V-shape being convex toward one or the other side in the longitudinal direction X, as viewed in both of the first direction D1 and the second direction D2.

One polygonal annular portion 311 is arranged such that the pair of bent portions 312 are bent so as to be convex toward one side in the longitudinal direction X in the middle of first direction D1, and the pair of bent portions 313 are bent so as to be convex toward the other side in the longitudinal direction in the middle of the second direction D2. Another polygonal annular portion 311 arranged adjacent to the one polygonal annular portion 311 is bent at the pair of bent portions 312 and the pair of bent portions 313 to the other side of the one polygonal annular portion 311; the pair of bent portions 312 are bent so as to be convex toward the other side in the longitudinal direction X in the middle of the first direction D1; and the pair of bent portions 313 are bent so as to be convex toward one side in the longitudinal direction in the middle of second direction D2.

The three-dimensional portion 31 is formed by connecting the pair of bent portions 313 of the adjacent polygonal annular portions 311 with a tubular connecting portion 32 in the middle of the second direction D2, in a state in which mutual convex portions of the pair of bent portions 313 of the adjacent polygonal annular portions 311 face each other. The inner concave portion of the adjacent polygonal annular portions 311 is formed into a substantially diamond shape as viewed in the second direction D2.

The inner stent body 3 is configured by connecting the plurality of three-dimensional portions 31 side by side in the longitudinal direction X. The adjacent three-dimensional portions 31 are connected by connecting the pair of bent portions 312 of the adjacent polygonal annular portions 311 with the tubular connecting portion 32 in the middle of the first direction D1, in a state in which mutual convex portions of the pair of bent portions 312 of the adjacent polygonal annular portions 311 are arranged to face each other. The inner concave portion of the polygonal annular portions 311 of the adjacent three-dimensional portions 31 is formed into a substantially diamond shape as viewed in the first direction D1.

The inner stent body 3 described above is configured to have a mesh of a plurality of substantially diamond-shapes, with synthetic resin fiber configuring the plurality of polygonal annular portions 311, by connecting the plurality of polygonal annular portions 311. As described above, the inner stent body 3 is formed by connecting the plurality of polygonal annular portions 311 side by side in the longitudinal direction X of the inner stent body 3, in a state in which the polygonal annular portions 311 formed of synthetic resin fiber into a polygonal annular shape as viewed in the longitudinal direction X are bent so as to be convex in the longitudinal direction X.

The inner stent body 3 is configured so as to be deformable between the reduced diameter state and the expanded diameter state. Here, the pair of adjacent polygonal annular portions 311 are connected such that the mutual convex portions made of synthetic resin fiber of the adjacent polygonal annular portions 311 are connected to each other with the tubular connecting portion 32 connecting the pair of bent portions 312, and the mutual convex portions made of synthetic resin fiber of the adjacent polygonal annular portions 311 are connected to each other with the tubular connecting portion 32 connecting the pair of bent portions 313. Therefore, the synthetic resin fiber forming the polygonal annular portion 311 is applied with a force to restore the bent portion of the tubular connecting portion 32 to a linear shape (the arrows in FIG. 2). As a result, the synthetic resin fiber bent at the tubular connecting portion 32 is applied with a force to restore to the linear shape extending in the first direction D1 and the second direction D2 (direction intersecting with the longitudinal direction X of the inner stent body 3). Therefore, a radially expanding force is applied to the inner stent body 3, whereby the inner stent body 3 can stably press a stenotic site.

The number of peaks and valleys of the polygonal annular portions 311 configuring the three-dimensional portions 31 of the inner stent body 3 is about four to eight in the case of the stent for the small intestine, for example. In the present embodiment, the polygonal annular portion 311 is formed of large-diameter fiber into a square shape as viewed in the longitudinal direction X of the inner stent body 3, in which the number of peaks and valleys of the polygonal annular portions 311 is four, for example.

The shape of the inner stent body 3 is not limited in particular; for example, a structure is conceivable, in which synthetic resin fiber (fiber) is processed into a zigzag shape and connected in the longitudinal direction. In the case of the zigzag shape, the number of peaks and valleys of the zigzag shape is not limited in particular, but is preferably four to eight.

The pair of end flare portions 4 are connected at the ends of the inner stent body 3 in the longitudinal direction X, respectively, and formed into a zigzag shape of a polygonal annular structure having more peaks and valleys than the polygonal annular portion 311 of the inner stent body 3. The pair of end flare portions 4 are arranged outside in the longitudinal direction X of the outer stent 5 so as to abut on a normal site. The end flare portions 4 extending in the first direction D1 intersecting with the longitudinal direction X of the inner stent body 3 are formed larger in diameter than the inner stent body 3, and deformable from the reduced diameter state to the expanded diameter state. The end flare portions 4 are alternately formed side by side in a direction in which the peaks and valleys intersect with the longitudinal direction X of the inner stent body 3.

The end flare portions 4 are connected at the ends of the inner stent body 3 with the tubular connecting portions 32, at the bent portions 412 which are convex toward the inner stent body 3 side.

Since the end flare portions 4 abut on a normal site, trackability or restorability in relation to peristaltic movement of the gastrointestinal tract such as the intestinal tract is important. Therefore, the end flare portion 4 is formed of synthetic resin fiber having a diameter smaller than that of the inner stent body 3. The end flare portion 4 is configured into a polygonal annular structure being more polygonal than the polygonal annular portion 311 of the inner stent body 3 as viewed in the longitudinal direction X, and formed into a zigzag shape having a plurality of peaks and valleys configured with the plurality of bent portions 412 and 413 of the polygonal annular structure as viewed in the second direction D2.

The end flare portion 4 is formed into a zigzag shape of a polygonal annular structure having more peaks and valleys than the polygonal annular portion 311 of the inner stent body 3. Assuming that the number of peaks and valleys of the inner stent body 3 is a, the number of peaks and valleys of the end flare portion 4 is preferably na (n: integer), and more preferably 2n. In the present embodiment, the number of peaks and valleys of the polygonal annular structure of the end flare portion 4 is eight, for example. The end flare portion 4 may be provided at the ends of the inner stent body 3 or may be provided at only one end thereof.

The material of the synthetic resin fiber configuring the inner stent body 3 and the end flare portion 4 is not limited in particular; however, a material having a high degree of restorability is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of restorability. In particular, for example, polydioxanone (PDO) is preferably used as a material of the fiber configuring the inner stent body 3 and the end flare portion 4.

The synthetic resin fiber configuring the inner stent body 3 and the end flare portion 4 is not limited in particular, and may be monofilament yarn or multifilament yarn. From a perspective of enhancing the repulsive force against the pressure from the outer side of the inner stent body 3 in the radial direction at a stenotic site in vivo, the synthetic resin fiber configuring the inner stent body 3 is preferably monofilament yarn. The synthetic resin fiber configuring the inner stent body 3 and the end flare portion 4 may be twisted or may not be twisted.

The fiber diameter of the synthetic resin fiber configuring the inner stent body 3 and the end flare portion 4 described above is 0.05 mm to 0.7 mm, and preferably 0.4 mm to 0.6 mm, for example. The fiber diameter of the synthetic resin fiber configuring the end flare portion 4 is preferably the same as or smaller than the fiber diameter of the synthetic resin fiber configuring the inner stent body 3. The size of the inner stent body 3 is not limited in particular; for example, the diameter is 10 mm to 25 mm and the length is 30 mm to 250 mm in the expanded diameter state.

As illustrated in FIG. 3, the outer stent 5 is formed into a tubular structure extending in the longitudinal direction X (predetermined direction) by braiding synthetic resin fiber. As illustrated in FIG. 1, the outer stent 5 is arranged so as to cover the outer periphery of the inner stent body 3 of the inner stent 2. Since the synthetic resin fiber configuring the outer stent 5 has a diameter smaller than that of the inner stent body 3 of the inner stent 2, the outer stent 5 has a mesh denser than the mesh of the inner stent body 3 of the inner stent 2. The outer stent 5 is deformable from the reduced diameter state to the expanded diameter state.

The material of the synthetic resin fiber configuring the outer stent 5 is not limited in particular; however, a material having a high degree of rigidity is preferable. Examples of the biodegradable resin may include homopolymer, copolymer or blend polymer composed of L-lactic acid, D-lactic acid, DL-lactic acid, glycolic acid, ε-caprolactone or para-dioxanone. Non-biodegradable resin may also be used as long as the material has a high degree of rigidity. In particular, for example, poly-L-lactic acid (PLLA) is preferably used as a material of the fiber configuring the outer stent 5. In the present embodiment, the fiber configuring the outer stent 5 is formed from poly-L-lactic acid (PLLA), for example.

The shape of the outer stent 5 is not limited in particular; for example, the shape has a structure by braiding synthetic resin fiber. The end of the outer stent 5 is not limited in particular; and the end preferably has a shape with a high degree of self-expandability. The outer stent 5 may not have self-expandability, restorability, or trackability in relation to peristaltic movement.

In the case of placing the biodegradable stent 1 inside the gastrointestinal tract, the outer stent 5 in the compressed state is placed inside the gastrointestinal tract. As a result, the outer stent 5 is expanded and placed inside the gastrointestinal tract. Thereafter, the inner stent 2 in the compressed state is placed inside the outer stent 5. Therefore, the inner stent 2 and the outer stent 5 are placed so as to overlap with each other, in a state in which the inner stent body 3 of the inner stent 2 is arranged inside the outer stent 5.

More specifically, the biodegradable stent 1 is placed inside the gastrointestinal tract by using the stent delivery system. The stent delivery system of the present embodiment includes an outer sheath member (outer tube) (not illustrated) to be inserted into the gastrointestinal tract, and a pushing member (not illustrated). The inner stent 2 and the outer stent 5 can be loaded into the outer sheath member. The outer stent 5 and the inner stent 2 in the compressed state are linearly arranged side by side in this order from the distal end side to the proximal end side inside the outer sheath member. The outer stent 5 and the inner stent 2 in this state are extruded in this order from the distal end side of the outer sheath member by the pushing member arranged to the proximal end side inside the outer sheath member. As a result, the outer stent 5 is firstly extruded from the distal end side of the outer sheath member, then expanded inside the gastrointestinal tract, and placed inside the gastrointestinal tract. Thereafter, the pushing member further pushes the inner stent 2, whereby the inner stent 2 is extruded from the distal end side of the outer sheath member, expanded inside the outer stent 5, and placed inside the outer stent 5.

As described above, in the case of placing the biodegradable stent 1, the outer stent 5 is placed first, then the inner stent 2 is placed inside the outer stent 5, whereby the inner stent body 3 of the inner stent 2 can press the outer stent 5 toward the gastrointestinal tract side, and the end flare portions 4 arranged outside the ends of the outer stent 5 in the longitudinal direction X can press the gastrointestinal tract.

Here, in relation to the biodegradable stent 1 of the present invention, a description will be provided on reasons why the outer stent 5 formed of synthetic resin fiber (small-diameter fiber) having a diameter smaller than that of the inner stent body 3 into a tubular structure having a dense mesh is arranged so as to cover the outer periphery of the inner stent body 3 formed of synthetic resin fiber having a large diameter (large-diameter fiber) into a tubular structure having a sparse mesh.

In the case of configuring a stent of synthetic resin such as biodegradable resin, fiber having a relatively small diameter is used, from a perspective of ensuring loadability into a delivery sheath. In this case, sufficient strength of the stent thus manufactured cannot be ensured.

Therefore, in the present invention, the stent 1 is configured by arranging the outer stent 5 formed of synthetic resin fiber (small-diameter fiber) having a diameter smaller than that of the inner stent body 3 into a tubular structure having a mesh denser than the mesh of the inner stent body 3, so as to cover the outer periphery of the inner stent body 3 formed of synthetic resin fiber having a large diameter (large-diameter fiber) into a tubular structure having a sparse mesh.

As a result, the inner stent body 3 formed of large-diameter fiber with a sparse mesh is arranged inside the outer stent 5 formed of small-diameter fiber with a dense mesh, whereby the inner stent body 3 presses the outer stent 5 from the inside of the outer stent 5. Therefore, the pressing force of the inner stent body 3 from the inside of the outer stent 5 can reinforce the strength of the outer stent 5 and ensure the strength of the biodegradable stent 1 in its entirety. The inner stent 2 formed of large-diameter fiber is configured with a sparse mesh, whereby loadability into a delivery sheath can be ensured.

The end flare portion 4 is arranged at the ends of the inner stent body 3 (portions abutting at a normal site), where trackability or restorability in relation to peristaltic movement of the gastrointestinal tract is important. The end flare portion 4 is formed into a polygonal annular structure having more peaks and valleys than the polygonal annular portion 311 of the inner stent body 3, by using synthetic resin fiber having a small diameter (small-diameter fiber), whereby the end flare portion 4 is easily deformable to increase the area of adhesion to the gastrointestinal tract, therefore the trackability or restorability in relation to peristaltic movement of the gastrointestinal tract can be improved. Even though the end flare portion 4 is configured into a polygonal annular structure having more peaks and valleys than the polygonal annular portion 311 of the inner stent body 3, since the end flare portion 4 is formed of synthetic resin fiber having a small diameter (small-diameter fiber), loadability into a delivery sheath can be ensured.

An example of manufacturing the biodegradable stent 1 will be briefly described. In the present manufacture example, the inner stent body 3 of the inner stent 2 was manufactured as follows: polydioxanone (PDO) having a fiber diameter of 0.5 mm was processed into a square shape (zigzag shape) (number of peaks and valleys: four) to manufacture the polygonal annular portion 311; and six consecutive polygonal annular portions 311 bent in different directions in the longitudinal direction X were alternately arranged in the longitudinal direction X to manufacture three consecutive three-dimensional portions 31, whereby the inner stent body 3 was manufactured. In this manner, the inner stent body 3 having a core rod diameter of 20 mm was manufactured. The end flare portion 4 of the inner stent 2 was manufactured into a zigzag shape having a polygonal annular structure (number of peaks and valleys: eight) with the same material and fiber diameter as the inner stent body 3, and was connected at the ends of the inner stent body 3. The outer stent 5 was manufactured by braiding PLLA fibers (0.25 mm and 0.3 mm). The inner stent 2 was arranged inside the outer stent 5, and the outer stent 5 was placed as overlapping the outer side of the inner stent 2, whereby the biodegradable stent 1 was manufactured.

According to biodegradable stent 1 of the present embodiment described above, the following effects can be achieved.

(1a) The biodegradable stent 1 is configured to include: the inner stent 2 including the inner stent body 3 formed of synthetic resin fiber into a tubular structure having a mesh, the inner stent 2 being deformable from the reduced diameter state to the expanded diameter state; and the outer stent 5 formed into a tubular structure having a mesh denser than the mesh of the inner stent body 3, arranged so as to cover the outer periphery of the inner stent body 3, and deformable from the reduced diameter state to the expanded diameter state. Therefore, the inner stent body 3 formed with a sparse mesh is arranged inside the outer stent 5 formed with a dense mesh, whereby the pressing force of the inner stent body 3 from the inside of the outer stent 5 can reinforce the strength of the outer stent 5 and ensure strength of the biodegradable stent 1 in its entirety. As a result, the gastrointestinal tract can be pressed in the state in which the strength of the biodegradable stent 1 in its entirety is ensured by the pressing force of the inner stent body 3 from the inside of the outer stent 5, whereby the biodegradable stent 1 can be prevented from moving while preventing stenosis. Therefore, the biodegradable stent 1 capable of exerting self-expandability, restorability, adherence to the gastrointestinal tract, and trackability to peristaltic movement can be achieved.

(1b) The inner stent body 3 is formed by connecting the plurality of polygonal annular portions 311 side by side in the longitudinal direction X of the inner stent body 3, in a state in which the polygonal annular portions 311 formed of synthetic resin fiber into a polygonal annular shape as viewed in the longitudinal direction X are bent or curved so as to be convex in the longitudinal direction X. As a result, a simple configuration can achieve the biodegradable stent 1 capable of exerting self-expandability, restorability, adherence to the gastrointestinal tract, and trackability to peristaltic movement. The synthetic resin fiber forming the polygonal annular portion 311 is applied with a force to restore the bent portion of the tubular connecting portion 32 to a linear shape (the arrows in FIG. 2). As a result, the synthetic resin fiber bent at the tubular connecting portion 32 is applied with a force to restore to the linear shape extending in the direction intersecting with the longitudinal direction X of the inner stent body 3. Therefore, the inner stent body 3 can stably press a stenotic site.

(1c) The inner stent 2 further includes the end flare portions 4 connected at the ends of the inner stent body 3 in the longitudinal direction X and having a size larger in diameter than the inner stent body 3. As a result, the end flare portion 4 can stably press the gastrointestinal tract. Thus, the end flare portions 4 arranged at the ends of the inner stent body 3 in the longitudinal direction X allow the biodegradable stent 1 to be stably held in the gastrointestinal tract.

(1d) The end flare portion 4 formed of synthetic resin fiber having a diameter smaller than that of the inner stent body 3 is configured into a polygonal annular structure being more polygonal than the polygonal annular portion 311 of the inner stent body 3. As a result, the end flare portion 4 is easily deformable to increase the area of adhesion to the gastrointestinal tract, whereby the trackability or restorability in relation to gastrointestinal motility can be improved. The end flare portion 4 is formed of synthetic resin fiber having a small diameter (small-diameter fiber), whereby loadability into a delivery sheath can be ensured.

(1e) The stent delivery system for placing the biodegradable stent 1 in vivo includes: the outer sheath member capable of interiorly loading the inner stent 2 and the outer stent 5, in which the outer stent 5 and the inner stent 2 are arranged side by side in this order from the distal end side; and the pushing member arranged inside the outer sheath member and capable of extruding the outer stent 5 and the inner stent 2 in this order from the distal end side of the outer sheath member. As a result, the pushing member extrudes the outer stent 5 and the inner stent 2 in this order, whereby the biodegradable stent 1 can be easily placed inside the gastrointestinal tract.

Second Embodiment

Figure 4:
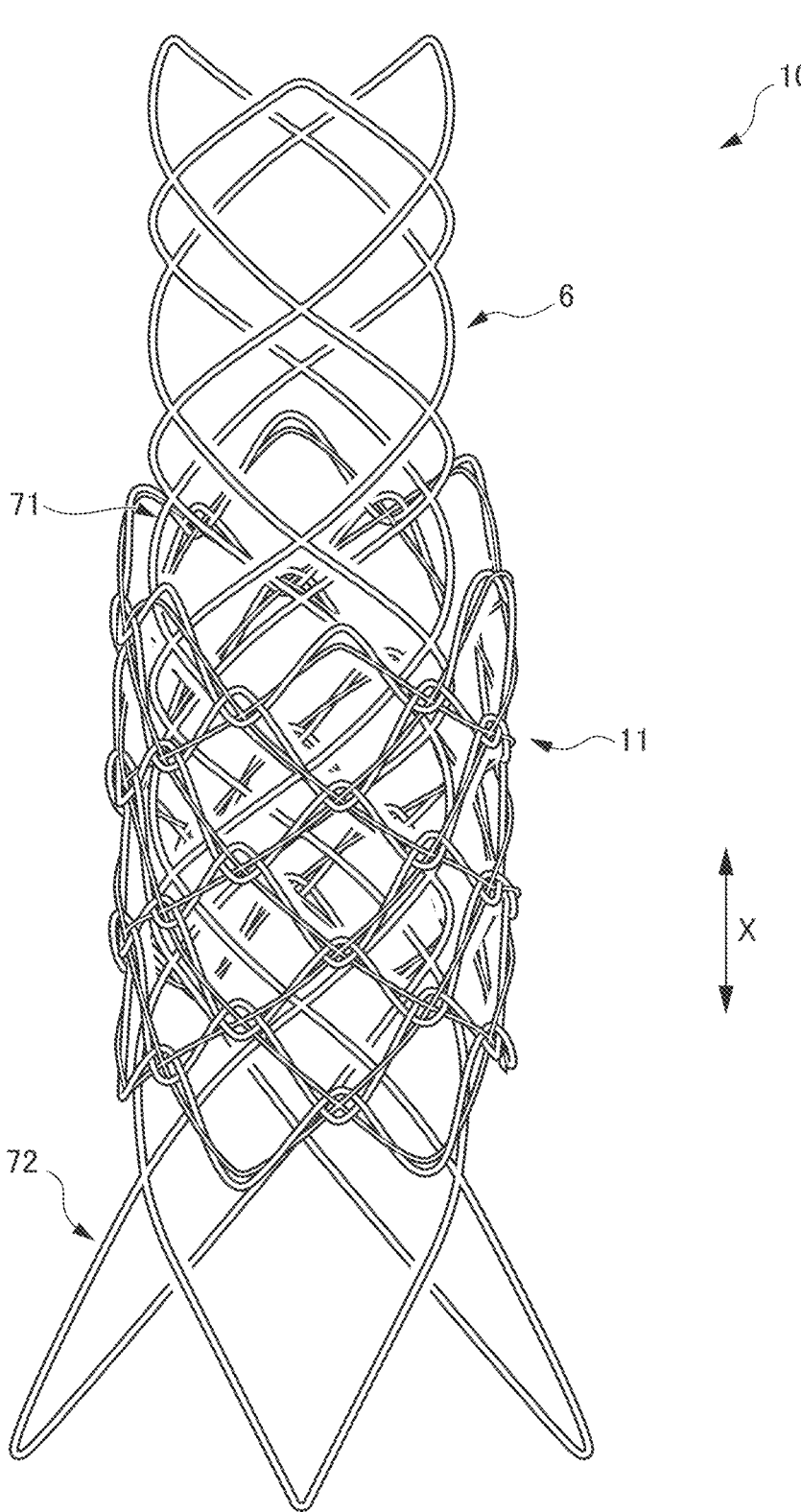
FIG. 4 is a perspective view illustrating a biodegradable stent according to a second embodiment.

Next, a second embodiment of the present invention will be described. FIG. 4 is a perspective view illustrating a biodegradable stent 10 according to the second embodiment. The biodegradable stent 10 of the second embodiment mainly differs in configuration of an inner stent 6 and an outer stent 11.

As illustrated in FIG. 4, the synthetic resin stent of the second embodiment is the biodegradable stent 10 composed of biodegradable fiber, and includes the inner stent 6 (first stent) and the outer stent 11 (second stent) arranged on the outer side of the inner stent 6. The central portion of the inner stent 6 in the longitudinal direction X (axial direction) is arranged inside the outer stent 11. The structures described in the first embodiment are omitted from description of the second embodiment. Similar to the biodegradable stent 1 of the first embodiment, the biodegradable stent 10 of the second embodiment is configured to include: the inner stent 6 including the inner stent body 71 formed of synthetic resin fiber into a tubular structure having a mesh, and deformable from the reduced diameter state to the expanded diameter state; and the outer stent 11 formed of synthetic resin fiber having a diameter smaller that of than the inner stent body 71 into a tubular structure having a mesh denser than the mesh of the inner stent body 71, the outer stent 11 arranged so as to cover the outer periphery of the inner stent body 3 and deformable from the reduced diameter state to the expanded diameter state.

Figure 5:
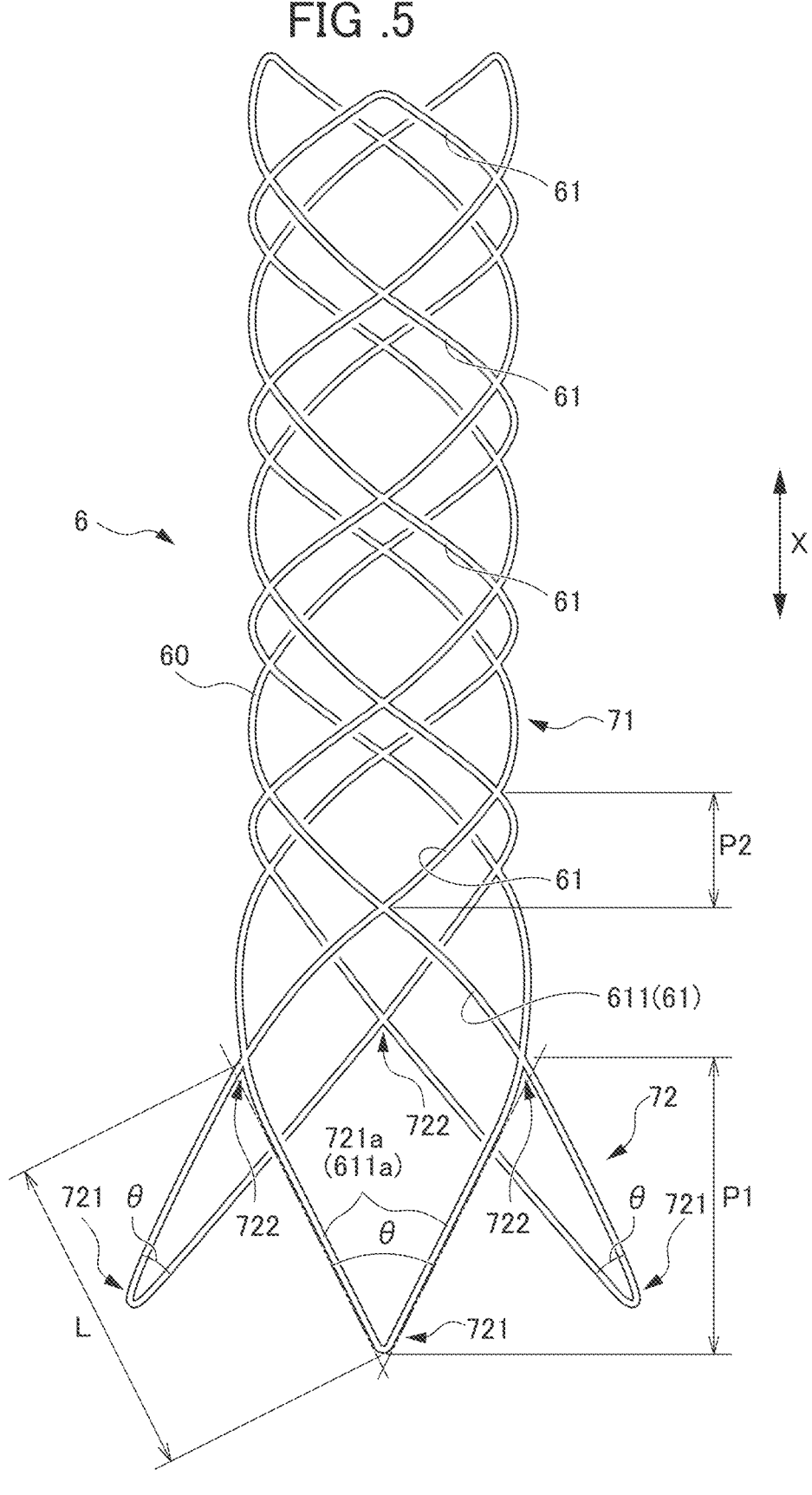
FIG. 5 is a perspective view illustrating an inner stent of the second embodiment.

The inner stent 6 will be described. FIG. 5 is a perspective view illustrating the inner stent 6 of the second embodiment. As illustrated in FIG. 5, the inner stent 6 of the present embodiment is a biodegradable stent composed of biodegradable fiber, formed as extending in the longitudinal direction X (axial direction) and deformable from the reduced diameter state to the expanded diameter state. FIG. 5 illustrates the inner stent 6 in a natural condition. The inner stent 6 can deform from the natural state illustrated in FIG. 5 to the reduced diameter state; and when the inner stent 6 in the reduced diameter state is placed inside the gastrointestinal tract, the inner stent 6 deforms from the reduced diameter state to the expanded diameter state, depending on the size of the gastrointestinal tract.

The inner stent 6 is woven into a mesh of a plurality of fibers 60 (wires) and formed into a tubular structure, and includes a multitude of grids 61 formed of the fibers 60 on the outer periphery and configured with argyle voids arranged in an orderly fashion. The plurality of grids 61 are arranged side by side in the axial direction and arranged side by side in the circumferential direction. The mesh of the inner stent 6 becomes sparse in the axial direction when the inner stent 6 is in the reduced diameter state, and becomes dense in the axial direction when the inner stent 6 is in the expanded diameter state. In the present embodiment, intersecting points between the woven fibers 60 are fixed. Examples of a fixing method may include an adhesion method or an ultrasonic welding method. At least, adjacent peaks 721 of an end flare portion 72 to be described later are fixed at an intersecting point (intersection) to the most end-side in the axial direction. In the present embodiment, the inner stent 6 is fixed at all of the intersecting points at which the woven fibers 60 intersect. As a result, compressive strength of the inner stent 6 can be improved. The intersecting point at which the adjacent peaks 721 of the end flare portion 72 are fixed may be fixed by intersecting with two linear fibers 60 or may be fixed by fixing apices of the bent portions composed of two bent fibers 60.

The inner stent 6 includes the inner stent body 71 (first stent body) formed as extending in the longitudinal direction X in its entirety; and the end flare portion 72 arranged at one end of the inner stent 6 in the longitudinal direction X (axial direction). The inner stent 6 is placed inside the gastrointestinal tract, in a state in which a portion of the inner stent body 71 is arranged inside the outer stent 11, and the end flare portion 72 is not covered by the outer stent 11.

The inner stent body 71 is formed into a tubular structure having a mesh with the plurality of grids 61. The plurality of grids 61 are arranged side by side in the axial direction and arranged side by side in the circumferential direction. In the present embodiment, the plurality of grids 61 are configured with argyle voids, respectively.

In the present embodiment, the end flare portion 72 is only provided at one end side of the inner stent 6 in the longitudinal direction. Since the end flare portion 72 abuts at a normal site of the gastrointestinal tract, trackability or restorability in relation to peristaltic movement of the gastrointestinal tract such as the intestinal tract is important, and it is important that post-placement migration due to peristaltic movement of the gastrointestinal tract can be suppressed. In the present embodiment, the end flare portion 72 is only arranged at one end of the inner stent 6 in the axial direction, but is not limited thereto, and may be arranged at the ends of the inner stent 6 in the axial direction.

The plurality of peaks 721 composed of tip corners protruding outward in the axial direction are consecutively arranged at one end of the inner stent 6 in the circumferential direction, whereby the end flare portion 72 is formed into an annular shape as viewed in the axial direction. More specifically, the plurality of peaks 721 are each formed by bending the fiber 60 at the end of the inner stent 6. The number of the plurality of peaks 721 is preferably three to eleven, for example. In the present embodiment, the number of the plurality of peaks 721 is three, for example.

Two sides 721a and 721a of the peak 721 are composed of two sides 611a and 611a of the end grid 611 arranged at the end in the axial direction, among the plurality of grids 61 arranged side by side in the axial direction.

The end flare portion 72 is formed such that a tip angle θ (angle) formed by the two sides 611a and 611a of the end grid 611 configuring the two sides 721a and 721a of the peak 721 is 80° or less in the state in which the inner stent 6 is placed inside the gastrointestinal tract. The reason why the tip angle θ formed by the two sides 721a and 721a of the peak 721 is set to 80° or less is based on the result of the evaluation test described later. As described later in the result of the evaluation test, in the case in which the tip angle θ formed by the two sides 721a and 721a of the peak 721 is 80° or less, post-placement migration of the inner stent 6 due to peristaltic movement of the gastrointestinal tract is 1 cm or less, after repeating movement simulating peristaltic movement 10 times.

In the present embodiment, the end flare portion 72 is configured such that the tip angle θ formed by the two sides 721a and 721a of the peak 721 is 80° or less in the state in which the inner stent 6 is placed inside the gastrointestinal tract, and the plurality of peaks 721 are consecutively arranged in the circumferential direction such that the number of the plurality of peaks 721 is three to eleven. The shape of the end flare portion 72 configured as described above is determined such that: the number of the peaks 721 arranged in the circumferential direction and the tip angle θ formed by the two sides 721a and 721a of the peak 721 determine the density in the circumferential direction and the protrusion length of the tip corners of the peaks 721; and the plurality of peaks 721 composed of the tip corners protruding outward in the axial direction are consecutively arranged in the circumferential direction in a relatively sparse state. In the present embodiment, the end flare portion 72 is configured such that the ends of the inner stent 6 are woven sparser than the inner stent body 71. As described later in the result of the evaluation test, post-placement migration of the inner stent 6 due to peristaltic movement of the gastrointestinal tract is 1 cm or less; therefore, the end flare portion 72 thus configured can achieve trackability to peristaltic movement of the gastrointestinal tract, and can suppress post-placement migration due to peristaltic movement of the gastrointestinal tract.

As illustrated in FIG. 5, in the present embodiment, an axial distance (amplitude) between the apex of the peak 721 and the apex of the valley 722 of the end flare portion 72 is referred to as a pitch P1. An axial distance (amplitude) between the peaks protruding in the axial direction of the grid 61 of the inner stent body 71 is referred to as a pitch P2. The length of one side 721a among the two sides 721a and 721a configuring the peak 721 of the end flare portion 72 is referred to as one side length L. One side length L of one side 721a of the peak 721 is the length from the apex of the peak 721 to the apex of the valley 722.

In the inner stent 6 of the present embodiment, the pitch P1 of the end flare portion 72 is formed large, and the pitch P2 of the inner stent body 71 is formed smaller than the pitch P1 of the end flare portion 72. For example, the ratio of the pitch P1 of the end flare portion 72 to the pitch P2 of the inner stent body 71 (pitch P1/pitch P2) is preferably 3.3 to 7.0. As a result, the inner stent body 71 and the end flare portion 72 are formed without sharp change in pitch. The ratio of the pitch P1 of the end flare portion 72 to the pitch P2 of the inner stent body 71 (pitch P1/pitch P2) falls within a range of 3.3 to 7.0, whereby the trackability to peristaltic movement of the gastrointestinal tract can be improved. The end flare portion 72 is arranged at a normal site of the gastrointestinal tract, and the inner stent body 71 is arranged at a stenotic site of the gastrointestinal tract.

The reason why the end flare portion 72 is arranged at a normal site and the inner stent body 71 is arranged at a stenotic site will be described. In the case in which the pitch P1 of the stent is large, the peaks 721 become parallel to the gastrointestinal tract in the axial direction even at a site of the gastrointestinal tract having a larger diameter, whereby post-placement migration of the stent due to peristaltic movement of the gastrointestinal tract can be suppressed. In the case in which the pitch P1 of the stent is large, the mesh becomes sparse; therefore, the compressive strength decreases. Therefore, by increasing the pitch P1, post-placement migration of the stent due to peristaltic movement of the gastrointestinal tract can be suppressed, even at a site of the gastrointestinal tract having a large diameter. Here, the stent placed at a normal site is not required to have high compressive strength. Therefore, the stent having the large pitch P1 is preferably arranged at a normal site, in which the diameter of the gastrointestinal tract is large so that high compressive strength is not required.

On the other hand, in the case in which the pitch P2 of the stent is small, when the diameter of the gastrointestinal tract for placing the stent is small, the peaks 721 become close to parallel to the gastrointestinal tract in the axial direction, whereby post-placement migration of the stent due to peristaltic movement of the gastrointestinal tract can be suppressed. In the case in which the pitch P2 of the stent is small, the mesh becomes dense; therefore, compressive strength increases. Here, the stent placed at a stenotic site is required to have high compressive strength. Therefore, the stent having the small pitch P2 is preferably arranged at a stenotic site, in which the diameter of the gastrointestinal tract is small so that high compressive strength is required.

One side length L of one side 721a of the two sides 721a and 721a configuring the peak 721 of the end flare portion 72 preferably falls within a range of 16 mm to 22 mm, for example, based on the result of the evaluation test described later. In the case in which one side length L of one side 721a of the peak 721 of the end flare portion 72 falls within a range of 16 mm to 22 mm, for example, post-placement migration of the inner stent 6 due to peristaltic movement of the gastrointestinal tract is 1 cm or less, as described later in the result of the evaluation test, whereby trackability to peristaltic movement of the gastrointestinal tract can be achieved, and post-placement migration due to peristaltic movement of the gastrointestinal tract can be suppressed.

The material of the synthetic resin fibers 60 configuring the inner stent body 71 and the end flare portion 72 is not limited in particular; however, a material having a high degree of restorability is preferable. Examples of the biodegradable resin may include homopolymer, copolymer, or blend polymer composed of L-lactic acid, D-lactic acid, DL-lactic acid, glycolic acid, ε-caprolactone, para-dioxanone, or trimethylene carbonate. Non-biodegradable resin may also be used as long as the material has a high degree of restorability. In particular, for example, polydioxanone (PDO) is preferably used as a material of the fiber configuring the inner stent body 71 and the end flare portion 72.

In the present embodiment, the inner stent 6 may be configured by connecting the axially extending fiber of a zigzag shape in the circumferential direction, or may be configured by weaving a single fiber, for example.

The synthetic resin fiber configuring the inner stent body 71 and the end flare portion 72 is not limited in particular, and may be monofilament yarn or multifilament yarn. From a perspective of enhancing the repulsive force against the pressure from the outer side in the radial direction of the inner stent body 71 at a stenotic site in vivo, the synthetic resin fiber configuring the inner stent body 71 is preferably monofilament yarn.

The fiber diameter (diameter) of the synthetic resin fiber configuring the inner stent body 71 and the end flare portion 72 is 0.05 mm to 0.7 mm, and preferably 0.4 mm to 0.6 mm, for example. The diametrical size of the inner stent body 71 is not limited in particular; however, for example, the diameter is 10 mm to 25 mm and the length is 30 mm to 250 mm in the expanded diameter state.

In the case in which the diameter of the abutting gastrointestinal tract is φ 16 mm to φ 20 mm, the pitch P1 of the end flare portion 72 is preferably 12 mm or more. In the case in which the diameter of the abutting gastrointestinal tract is about φ 12 mm, the pitch P2 of the inner stent body 71 is preferably 3 mm or more.

The diameter of the inner stent body 71 of the inner stent 6 is formed slightly larger in diameter (e.g., by about 10 to 20%) than the target gastrointestinal tract. In the case in which the inner stent 6 is placed inside the gastrointestinal tract, the inner stent 6 in the reduced diameter state is placed inside the target gastrointestinal tract and expanded after placement.

For example, in the case in which the inner stent 6 is placed inside the gastrointestinal tract having a diameter of φ 16 mm, the diameter of the inner stent body 71 of the inner stent 6 to be placed is preferably 17 mm to 32 mm in a natural state, for example. Three to eleven of the peaks 721 are preferably consecutively arranged in the circumferential direction of the end flare portion 72 of the inner stent 6 to be placed, in which one side length L of one side 721a among the two sides 721a and 721a configuring the peak 721 is preferably 16 mm to 22 mm. In the end flare portion 72, the angle formed by the two sides 721a and 721a configuring the peak 721 is preferably 38.5° to 147.3° in a natural state, for example, and the angle formed by the two sides 721a and 721a configuring the peak 721 is preferably 36.2° to 78.4° after placing the inner stent 6 inside the gastrointestinal tract, for example.

Here, referring to FIGS. 6 to 8, the result of the evaluation test using the inner stent 6 of the present embodiment will be described. In the present evaluation test, the inner stent 6 illustrated in FIG. 5 including the inner stent body 71 and the end flare portion 72 arranged at one end side was manufactured using monofilaments of polydioxanone (PDO) having a fiber diameter of 0.4 mm or 0.5 mm, by changing each parameter (number of peaks, pitch P1, tip angle θ, and one side length L). The end flare portion 72 was formed by consecutively arranging the plurality of peaks 721 side by side in the circumferential direction at the end of the inner stent 6.

For example, in the present evaluation test, the inner stent 6 was manufactured using fiber having a fiber diameter of 0.4 mm, such that the parameters (number of peaks, pitch P1, tip angle θ, and one side length L) will be as illustrated in (a) of FIG. 6, in the state of being placed inside the intestinal tract of φ 16 mm. Here, the diameter of the inner stent 6 is reduced when placed inside the intestinal tract; therefore, the inner stent 6 attached to a core rod of φ 20 mm is manufactured, and the inner stent 6 thus manufactured is placed in the intestinal tract of φ 16 mm.

For example, as illustrated in the upper table of (a) of FIG. 6, in the case of manufacturing the inner stent 6 having three peaks in which the pitch P1 of the end flare portion 72 in the placed state is 7.0 mm, 8.7 mm, 11.0 mm, 11.8 mm, 13.5 mm, 16.3 mm, 19.0 mm, or 22.0 mm, the inner stent 6 having the pitch P1 smaller than the pitch P1 when attached to the core rod of φ 20 mm needs to be manufactured; therefore, as illustrated in (b) of FIG. 6, the inner stent 6 having the pitch P1 of 3.0 mm, 6.0 mm, 9.0 mm, 10.0 mm, 12.0 mm, 15.0 mm, 18.0 mm, or 21.0 mm will be manufactured. As illustrated in the lower table of (a) of FIG. 6, in the case of manufacturing the biodegradable stent having four peaks in which the pitch P1 of the end flare portion 72 in the placed state is 5.6 mm, 7.7 mm, 10.1 mm, 11.0 mm, 12.8 mm, 15.7 mm, 18.7 mm, or 21.5 mm, the inner stent 6 having the pitch P1 smaller than the pitch P1 when attached to the core rod of φ 20 mm needs to be manufactured; therefore, as illustrated in (b) of FIG. 6, the inner stent 6 having the pitch P1 of 3.0 mm, 6.0 mm, 9.0 mm, 10.0 mm, 12.0 mm, 15.0 mm, 18.0 mm, or 21.0 mm will be manufactured.

In this case, the pitch P1 and the number of peaks can be used to calculate a theoretical value of "tip angle" as illustrated in (a) and (b) of FIG. 6. One side length is the same length in the placed state and in the case of manufacturing a stent attached to a core rod.

As described above, in the present evaluation test, in the case of manufacturing the inner stent 6 using fiber having a fiber diameter of 0.4 mm, the parameters (number of peaks, pitch P1, tip angle θ, and one side length L) of the stent placed inside the intestinal tract of φ 16 mm were calculated to provide the theoretical values of the parameters (number of peaks, pitch P1, tip angle θ, and one side length L) of the stent attached to the core rod of φ 20 mm. The fiber was attached to the core rod of φ 20 mm to manufacture the inner stent 6 before placement so as to provide the values (theoretical values) of the parameters (number of peaks, pitch P1, tip angle θ, and one side length L) of the stent attached to the core rod of φ 20 mm.

The present evaluation test was conducted using the stent manufactured as described above. As a testing method, the inner stent 6 manufactured by changing the parameters (number of peaks, pitch P1, tip angle θ, and one side length L) was placed inside a polyethylene tube having an inner diameter of 16 mm or 20 mm, and movement simulating peristaltic movement was applied to the polyethylene tube. The movement simulating peristaltic movement was repeated 10 times for the inner stent 6 placed inside the gastrointestinal tract, in which the polyethylene tube was moved in one direction and returned, then migration of the stent from the initial position was measured.

An evaluation result illustrated in FIGS. 7 and 8 will be described. FIGS. 7 and 8 illustrate the evaluation results, in which the inner stent 6 was manufactured using fiber having a fiber diameter of φ 0.4 mm or φ 0.5 mm, having three or four peaks 721 of the end flare portion 72, by changing the one side length L of one side 721a among the two sides 721a and 721a of the end flare portion 72 as well as the tip angle θ, then the inner stent 6 thus manufactured was used to measure a distance in post-placement migration of the end flare portion 72, and the results are listed in the tables. The values in the blank cells of FIGS. 7 and 8 were not actually measured but estimated from the values in cells neighboring the blank cells.

First, the evaluation result illustrated in FIG. 7 will be described. An evaluation result 1 illustrated in FIG. 7 is the evaluation result using fiber having a fiber diameter of φ 0.4 mm.

As illustrated in (a) of FIG. 7, in the case in which the number of the peaks was three, the one side length L1 of one side 721a of the peak 721 of the end flare portion 72 was in the range of 14.5 mm to 23.5 mm, and the tip angle θ formed by the two sides 721a configuring the peak 721 was in the range of 46.4° to 78.4°, the post-placement migration of the inner stent 6 was 1 cm or less. Therefore, the evaluation result thus obtained shows that, in the case in which the number of the peaks 721 is three, the one side length L1 of one side 721a of the peak 721 of the end flare portion 72 is preferably in the range of 14.5 mm to 23.5 mm, and the tip angle θ formed by the sides 721a and 721a configuring the peak 721 is preferably 78.4° or less.

As illustrated in (b) of FIG. 7, in the case in which the number of the peaks was four, the one side length L1 of one side 721a of the peak 721 of the end flare portion 72 was in the range of 16.9 mm to 22.4 mm, and the tip angle θ formed by the two sides 721a configuring the peak 721 was in the range of 36.2° to 61.4°, the post-placement migration of the inner stent 6 was 1 cm or less. Therefore, the evaluation result thus obtained shows that, in the case in which the number of the peaks is four, the one side length L1 of one side 721a of the peak 721 of the end flare portion 72 is preferably in the range of 16.9 mm to 22.4 mm, and the tip angle θ formed by the sides 721a and 721a configuring the peak 721 is preferably 61.4° or less.

Next, an evaluation result 2 illustrated in FIG. 8 will be described. FIG. 8 illustrates the evaluation result 2 using fiber having a fiber diameter of φ 0.5 mm.

As illustrated in (a) of FIG. 8, in the case in which the number of the peaks was three, the one side length L1 of one edge 721a of the peak 721 of the end flare portion 72 was in the range of 18.3 mm to 23.5 mm, and the tip angle θ formed by the two sides 721a configuring the peak 721 was in the range of 46.4° to 67.1°, the post-placement migration of the inner stent 6 was 1 cm or less. Therefore, the evaluation result thus obtained shows that, in the case in which the number of the peaks is three, the one side length L1 of one side 721a of the peak 721 of the end flare portion 72 is preferably in the range of 18.3 mm to 23.5 mm, and the tip angle θ formed by the two sides 721a and 721a configuring the peak 721 is preferably 67.1° or less.

As illustrated in (b) of FIG. 8, in the case in which the number of the peaks was four, the one side length L1 of one side 721a of the peak 721 of the end flare portion 72 was in the range of 12.7 mm to 22.4 mm, and the tip angle θ formed by the two sides 721a configuring the peak 721 was in the range of 36.2° to 65.9°, the post-placement migration of the inner stent 6 was 1 cm or less. Therefore, the evaluation result thus obtained shows that, in the case in which the number of the peaks is three, the one side length L1 of one side 721a of the peak 721 of the end flare portion 72 is preferably in the range of 12.7 mm to 22.4 mm, and the tip angle θ formed by the sides 721a and 721a configuring the peak 721 is preferably 65.9° or less.

The evaluation result 2 thus obtained shows that the tip angle θ formed by the two sides 721a and 721a of the peak 721 of the end flare portion 72 is preferably 78.4° or less; therefore, the tip angle θ is preferably 80° or less, for example. The evaluation result 2 thus obtained shows that the one side length L of one side 721a among the two sides 721a and 721a configuring the peak 721 of the end flare portion 72 is preferably in the range of 16.9 mm to 22.4 mm; therefore, the one side length L is preferably in the range of 16 mm to 22 mm, for example.

According to inner stent 6 of the present embodiment described above, the following effects can be achieved.

(2a) The inner stent 6 is configured to include the end flare portion 72 arranged at the end in the axial direction; the end flare portion 72 is formed into an annular shape as viewed in the axial direction by consecutively arranging the plurality of peaks 721 in the circumferential direction, the peaks 721 consisting of the tip corners protruding outward in the axial direction; the tip angle θ formed by the two sides 721a and 721a configuring the peak 721 is 80° or less in the state in which the inner stent 6 is placed inside the gastrointestinal tract; and the number of the plurality of peaks 721 is three to eleven. As a result, as shown in the result of the evaluation test, the post-placement migration of the inner stent 6 due to peristaltic movement of the gastrointestinal tract is 1 cm or less; therefore, trackability to peristaltic movement of the gastrointestinal tract can be achieved, and post-placement migration of the inner stent 6 due to peristaltic movement of the gastrointestinal tract can be suppressed.

(2b) The two sides 721a and 721a configuring the peak 721 of the end flare portion 72 are configured with the two sides 611a and 611a of the end grid 611 arranged at the end in the axial direction. As a result, the end grid 611 is formed into a grid shape to have compressive strength; therefore, the compressive strength of the peaks 721 can be enhanced. Therefore, post-placement migration of the inner stent 6 due to peristaltic movement of the gastrointestinal tract can be further suppressed, in the state in which the compressive strength of the end flare portion 72 is ensured.

(2c) The inner stent 6 includes the plurality of grids 61 arranged side by side in the axial direction, and the end grid 611 is arranged at the end of the plurality of grids 61. As a result, compressive strength of the inner stent 6 in its entirety can be ensured, while post-placement migration of the inner stent 6 due to peristaltic movement of the gastrointestinal tract can be further suppressed at the end flare portion 72.

(2d) The one side length of one side 721a of the two sides 721a and 721a configuring the peak 721 is 16 mm to 22 mm. As a result, as shown in the result of the evaluation test, the post-placement migration of the inner stent 6 due to peristaltic movement of the gastrointestinal tract is 1 cm or less; therefore, trackability to peristaltic movement of the gastrointestinal tract can be achieved, and post-placement migration of the inner stent 6 due to peristaltic movement of the gastrointestinal tract can be further suppressed.

(2e) Adjacent peaks 721 of the end flare portion 72 are fixed at the intersecting point to the most end-side in the axial direction. As a result, post-placement migration of the inner stent 6 due to peristaltic movement of the gastrointestinal tract can be further suppressed, in the state in which the compressive strength of the end flare portion 72 is ensured.

In relation to the inner stent 6, in the present embodiment, for example, the number of the peaks 721 of the synthetic resin stent 6 is three or four, but is not limited thereto. The number of the peaks 721 of the synthetic resin stent 6 is preferably three to eight in the case of applying the synthetic resin stent 6 to a stent for the small intestine, for example, and preferably from three to eleven in the case of applying the synthetic resin stent 6 to a stent for the esophagus, for example.

Figure 9:
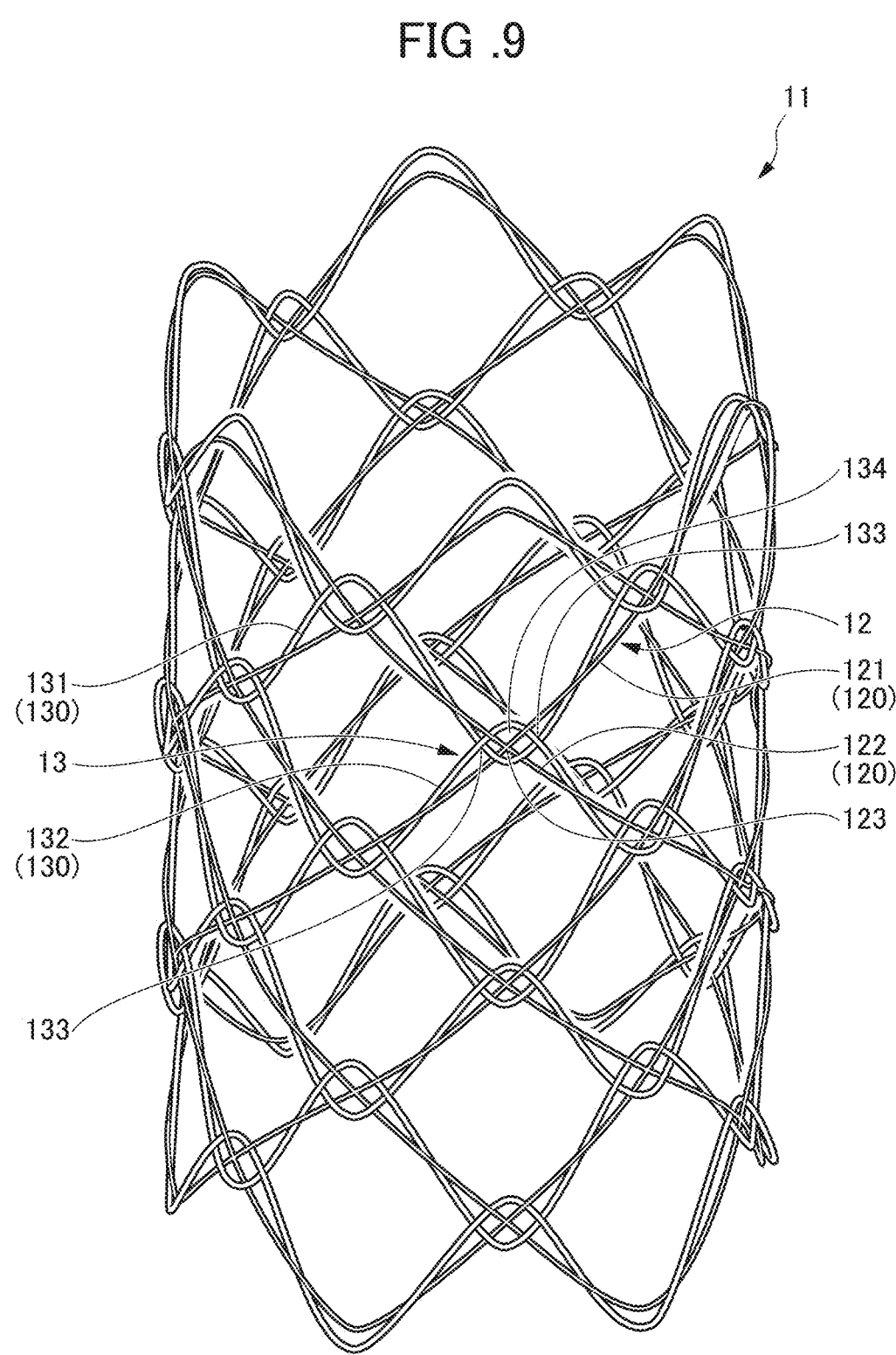
FIG. 9 is a perspective view illustrating an outer stent of the second embodiment.
Figure 10:
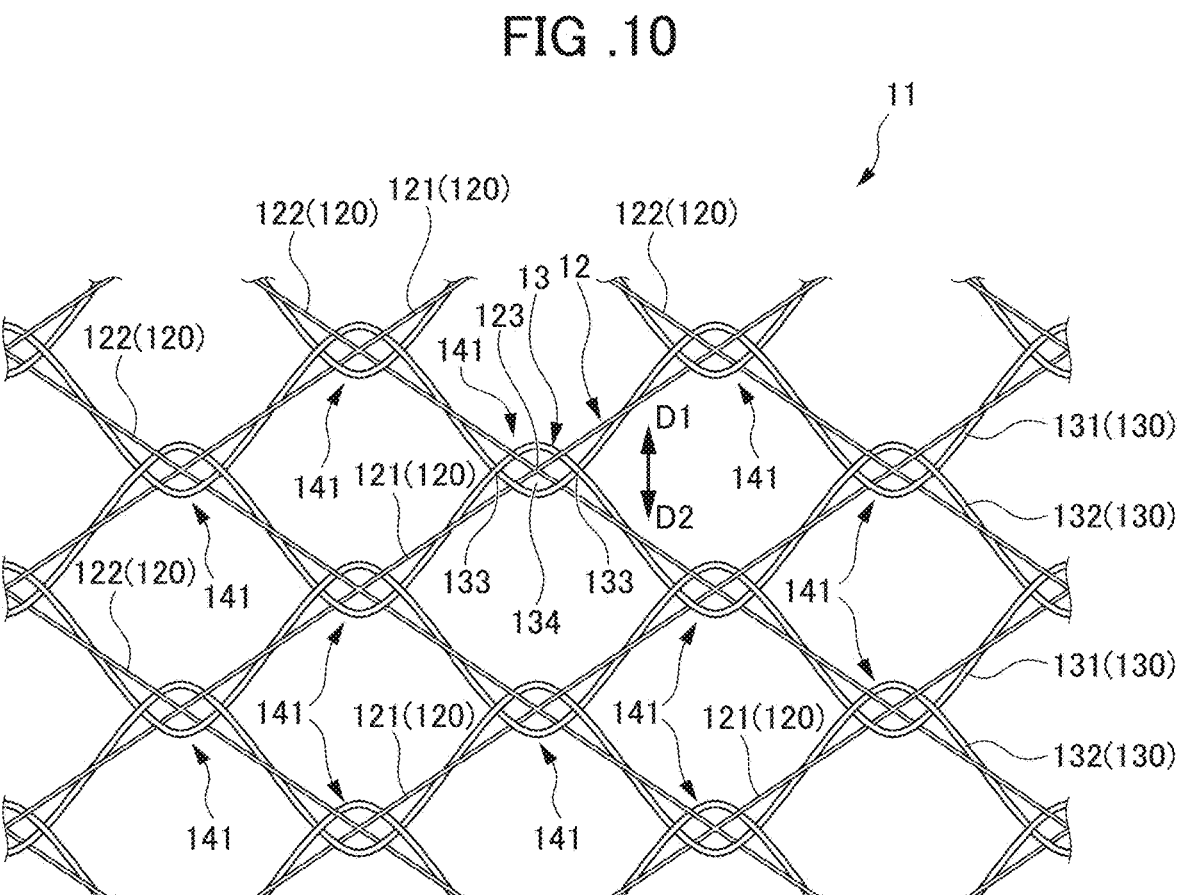
FIG. 10 is an enlarged view of the outer stent illustrated in FIG. 9.

Next, the outer stent 11 will be described. FIG. 9 is a perspective view illustrating the outer stent 11 of the second embodiment. FIG. 10 is an enlarged view of the outer stent 11 illustrated in FIG. 9. The outer stent 11 of the present embodiment is a biodegradable stent composed of biodegradable fiber, and includes a meshed tubular portion 12 (first woven component portion) and a wavily woven portion 13 (second woven component portion) arranged so as to be woven in the meshed tubular portion 12, as illustrated in FIGS. 9 and 10.

The meshed tubular portion 12 is woven into a mesh of a plurality of fibers 120 and configured into a tubular structure, and includes a multitude of argyle voids formed of the fibers 120 on the outer periphery and arranged in an orderly fashion. The mesh of the meshed tubular portion 12 becomes sparse in the axial direction when the outer stent 11 is in the reduced diameter state, and becomes dense in the axial direction when the outer stent 11 is in the expanded diameter state.

In the present embodiment, as illustrated in FIG. 10, the plurality of fibers 120 configuring the meshed tubular portion 12 includes a plurality of first fibers 121 and a plurality of second fibers 122. As viewed from the side, the meshed tubular portion 12 includes a multitude of argyle voids formed of the first fibers 121 and the second fibers 122, and includes a plurality of first intersecting points 123 configured by intersections of the plurality of first fibers 121 and the plurality of second fibers 122.

The plurality of first fibers 121 are formed of synthetic resin fiber extending so as to be inclined at a predetermined angle with respect to the axial direction. In the present embodiment, as illustrated in FIG. 10, the plurality of first fibers 121 are arranged so as to be inclined and extending from the upper right side to the lower left side.

The plurality of second fibers 122 are formed of synthetic resin fiber extending so as to intersect with the plurality of first fibers 121. In the present embodiment, as illustrated in FIG. 10, the plurality of second fibers 122 are arranged so as to be inclined and extending from the upper left side to the lower right side.

The material of the first fibers 121 and the second fiber 122 is not limited; however, a material having a high degree of rigidity is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of rigidity. In particular, for example, poly-lactic acid (PLA) or poly-L-lactic acid (PLLA) is preferably used as the material of the fiber configuring the first fibers 121 and the second fiber 122. In the present embodiment, the first fibers 121 and the second fiber 122 are formed from polylactic acid (PLA), for example.

In the case of using biodegradable fiber as the fiber 120, the diameter thereof is preferably 0.1 mm to 0.4 mm. When the diameter of the biodegradable fiber 120 is less than 0.1 mm, the strength of the outer stent 11 tends to decrease. When the diameter of the biodegradable fiber 120 exceeds 0.4 mm, the diameter increases in the reduced diameter state, so that it tends to be difficult to load the outer stent 11 into a fine tubular member such as a delivery system. The upper limit of the diameter of the biodegradable fiber 120 is further preferably 0.3 mm, from a perspective of loading into a delivery system having a small inner diameter. The lower limit of the diameter of the biodegradable fiber 120 is more preferably 0.2 mm, from a perspective of maintaining high strength. In the present embodiment, biodegradable fiber having a diameter of 0.2 mm and biodegradable fiber having a diameter of 0.3 mm are used as the fibers 120.

As illustrated in FIG. 9, the plurality of annularly formed wave-shaped fibers 130 of the wavily woven portion 13 are arranged so as to be woven in the meshed tubular portion 12. In the present embodiment, the plurality of fibers 130 configuring the wavily woven portion 13 include: a plurality of third fibers 131 arranged so as to be spaced apart in the axial direction; and a plurality of fourth fibers 132 arranged so as to be spaced apart in the axial direction. The wavily woven portion 13 includes a plurality of second intersecting points 133 formed by intersections of the plurality of third fibers 131 and the plurality of fourth fibers 132.

As illustrated in FIG. 10, the third fibers 131 and the fourth fibers 132 are formed into a wave shape extending in the circumferential direction of the meshed tubular portion 12, in which peaks and valleys consecutively alternate. The third fibers 131 and the fourth fibers 132 are arranged such that the mutual convex portions face each other and the facing convex portions partly overlap with each other.

More specifically, the third fibers 131 and the fourth fibers 132 are formed into a wave shape having peaks convex toward the first direction D1 side and peaks convex toward the second direction D2 side, in which mutual peaks partly overlap with each other and intersect at two second intersecting points 133, as viewed from the side. The wavily woven portion 13 includes an intersecting region 134 as viewed from the side. The intersecting region 134 is a region surrounded by the third fiber 131 and the fourth fiber 132 between the two adjacent second intersecting points 133 among the plurality of second intersecting points 133, where the mutual convex portions of the third fiber 131 and the fourth fiber 132 overlap with each other. The plurality of intersecting regions 134 are formed side by side in the circumferential direction of the meshed tubular portion 12 being tubular.

The material of the synthetic resin fiber configuring the third fiber 131 and the fourth fiber 132 is not limited in particular; however, a material having a high degree of restorability is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of restorability. For example, polydioxanone (PDO) is preferably used as the material of the third fiber 131 and the fourth fiber 132.

In the case of using biodegradable fiber as the fiber 130, the diameter thereof is preferably 0.1 mm to 0.4 mm. In the present embodiment, the biodegradable fiber having a diameter of 0.15 mm to 0.22 mm is used as the fiber 130.

The first intersecting points 123 of the meshed tubular portion 12 are arranged in the plurality of intersecting regions 134 of the wavily woven portion 13, respectively, as the meshed tubular portion 12 is viewed from the side. The plurality of first intersecting points 123 are arranged in the plurality of intersecting regions 134, respectively, and arranged side by side in the circumferential direction of the meshed tubular portion 12 being tubular. The portion where the first intersecting point 123 of the meshed tubular portion 12 is arranged in the intersecting region 134 of the wavily woven portion 13 configures a first hooking portion 141. The outer stent 11 of the present embodiment includes the plurality of first hooking portions 141, in which a row of the plurality of first hooking portions 141 arranged side by side in the circumferential direction is formed throughout the axial direction.

In the first hooking portion 141, the third fiber 131 is arranged in the state of being hookable by one or more of the first fibers 121, the second fibers 122, and the fourth fibers 132, in relation to movement in a direction in which the mutually overlapping convex portion of the third fiber 131 and the fourth fiber 132 shrinks in size. The fourth fiber 132 is arranged in the state of being hookable by one or more of the first fibers 121, the second fibers 122, and the third fibers 131, in relation to movement in a direction in which the mutually overlapping convex portion of the third fiber 131 and the fourth fiber 132 shrinks in size.

In the present embodiment, the third fiber 131 and the fourth fiber 132 configuring the wavily woven portion 13 are formed of synthetic resin fiber having an expansion force higher than the first fibers 121 and the second fiber 122 configuring the meshed tubular portion 12; therefore, the bent portion thereof has a property of returning to a straight line. At least part of the third fiber 131 and the fourth fiber 132 is arranged so as to be woven in the meshed tubular portion 12, can apply a force to increase the diameter of the outer stent 11, and can deform the meshed tubular portion 12 from the reduced diameter state to the expanded diameter state.

The configuration of the first hooking portion 141 will be described. FIG. 10 is a view, in which the radial direction of the tubular outer stent 11 in FIG. 9 is rearranged along the direction perpendicular to the paper (direction penetrating the paper) of FIG. 10. Therefore, the inside of the outer stent 11 in the radial direction is the backside in the vertical direction of the paper of FIG. 10; and the outer side of the outer stent 11 in the radial direction is the frontside in the vertical direction of the paper of FIG. 10.

As illustrated in FIG. 10, the first fibers 121 and the second fibers 122 of the meshed tubular portion 12 decussate at the first intersecting point 123 in the first hooking portion 141.

The third fiber 131 is arranged on the frontside or backside in FIG. 10 with respect to the fourth fiber 132 (outer side or inner side of the outer stent 11 in the radial direction) at both of the two second intersecting points 133. As a result, the third fiber 131 and the fourth fiber 132 of the outer stent 11 are arranged in the state of not being mutually hookable, in relation to mutual movement toward the first direction D1 or the second direction D2.

The first intersecting point 123 of the first fiber 121 and the second fiber 122 is arranged in the intersecting region 134 surrounded by the third fiber 131 and the fourth fiber 132, in the overlapping convex portion between the third fiber 131 and the fourth fiber 132 of the wavily woven portion 13.

As illustrated in FIG. 10, the first fiber 121 is arranged so as to be inclined and extending from the upper right side to the lower left side in the intersecting region 134. From the upper right side toward the lower left side, the first fiber 121 passes the frontside of one of the third fiber 131 and the fourth fiber 132, intersects with the second fiber 122 at the first intersecting point 123, and passes the backside of the other one of the third fiber 131 and the fourth fiber 132. As illustrated in FIG. 10, the second fiber 122 is arranged so as to be inclined and extending from the upper left side to the lower right side in the intersecting region 134. The second fiber 122 passes the frontside of one of the third fiber 131 and the fourth fiber 132, intersects with the first fiber 121 at the first intersecting point 123, and passes the backside of the other one of the third fiber 131 and the fourth fiber 132.

The first fiber 121, the second fiber 122, the third fiber 131, and the fourth fiber 132 are arranged as described above, whereby, in the first hooking portion 141, one of the third fiber 131 and the fourth fiber 132 having a peak convex toward the first direction D1 is arranged in the state of being hookable by the first fiber 121 and the second fiber 122, in relation to movement in a direction in which the mutually overlapping convex portion of the third fiber 131 and the fourth fiber 122 shrinks in size; and the other one of the third fiber 131 and the fourth fiber 132 having a peak convex toward the second direction D2 opposite to the first direction D1 is arranged in the state of being hookable by the first fiber 121 and the second fiber 122, in relation to movement in a direction in which the mutually overlapping convex portion of the third fiber 131 and the fourth fiber 132 shrinks in size.

The outer stent 11 as described above may be manufactured by weaving the wavily woven portion 13 and then weaving the meshed tubular portion 12, or conversely, by weaving the meshed tubular portion 12 and then weaving the wavily woven portion 13. In the case of manufacturing the outer stent 11, for example, a tubular tool with a plurality of pins standing on a circumferential surface at a predetermined interval may be used, the fiber is hooked by the plurality of pins to weave the wavily woven portion 13, and then the fiber of the meshed tubular portion 12 passes through the intersecting region of the wavily woven portion 13, whereby the outer stent 11 can be manufactured.

The meshed tubular portion 12 of the outer stent 11 configured as described above is woven into a tubular structure with the first fiber 121 and the second fiber 122 inclined with respect to the axial direction, whereby the shape of the stent is maintained in the tubular structure. The wave-shaped wavily woven portion 13 is woven into the meshed tubular portion 12, and the wavily woven portion 13 (third fiber 131 and fourth fiber 132) is formed of synthetic resin fiber having an expansion force higher than the meshed tubular portion 12 (first fiber 121 and second fiber 122), and the bent portion thereof has a property of returning to a straight line. Therefore, the wavily woven portion 13 is woven into a wave shape so as to circle the meshed tubular portion 12 in the circumferential direction, whereby the wavily woven portion 13 can apply a force to increase the diameter of the outer stent 11, and can enhance the expansion force. Thus, the expansion force of the outer stent 11 in the radial direction can be strengthened to achieve self-expandability. Adherence to the wall of the gastrointestinal tract can be increased, and trackability to gastrointestinal motility can be achieved.

The outer stent 11 is formed into a tubular structure extending in the longitudinal direction X (predetermined direction) by braiding synthetic resin fiber. The outer stent 11 is arranged so as to cover the outer periphery of the central part of the inner stent 6 in the longitudinal direction X. The outer stent 11 is formed of synthetic resin fiber having a diameter smaller than that of the inner stent 6, and has a mesh denser than the mesh of the inner stent 6. The outer stent 11 is deformable from the reduced diameter state to the expanded diameter state.

In the case of placing the biodegradable stent 10 inside the gastrointestinal tract, the outer stent 11 in the reduced diameter state is placed inside the gastrointestinal tract, and then expanded after placement. As a result, the outer stent 11 is expanded and placed inside the gastrointestinal tract. Thereafter, the inner stent 6 in the reduced diameter state is placed inside the outer stent 11 and expanded after placement. As a result, the inner stent 6 and the outer stent 11 are placed so as to overlap with each other, in the state in which the central side of the inner stent 6 is arranged inside the outer stent 11.

According to the outer stent 11 of the second embodiment described above, the following effects can be achieved.

(3a) The outer stent 11 is configured to include the meshed tubular portion 12 being tubular and composed of the plurality of fibers 121 and 122 woven into a mesh, and the wavily woven portion 13 composed of the plurality of fibers 131 and 132 annularly formed and woven into the meshed tubular portion 12; the meshed tubular portion 12 is configured to include the plurality of first fibers 121 extending so as to be inclined at a predetermined angle with respect to the axial direction, the plurality of second fibers 122 extending so as to intersect with the first fibers 121, and the plurality of first intersecting points 123 formed at intersections of the plurality of first fibers 121 and the plurality of second fibers 122; the wavily woven portion 13 is configured to include the plurality of wave-shaped third fibers 131 arranged so as to be spaced apart in the axial direction, and the plurality of wave-shaped fourth fibers 132 arranged so as to be spaced apart in the axial direction; and the at least one of the first intersecting points 123 is arranged in the intersecting region 134 surrounded by the third fibers 131 and the fourth fibers 132.

As a result, the meshed tubular portion 12 of the outer stent 11 is woven into a tubular structure with the first fibers 121 and the second fibers 122 inclined with respect to the axial direction, whereby the shape of the stent is maintained in the tubular structure. The wave-shaped wavily woven portion 13 is woven into the meshed tubular portion 12, and the first intersecting point 123 of the meshed tubular portion 12 is arranged in the intersecting region 134 of the wavily woven portion 13, whereby the wavily woven portion 13 can apply a force to increase the diameter and can enhance the expansion force in the radial direction. Thus, the expansion force of the outer stent 11 in the radial direction can be strengthened to achieve self-expandability. Adherence to the wall of the gastrointestinal tract can be increased, and trackability to gastrointestinal motility can be achieved. Therefore, the stent can ensure loadability into a fine tubular member such as a delivery system, in which migration of the stent is unlikely to occur after placement at the affected site of the natural tracts.

(3b) The plurality of intersecting regions 134 are formed side by side in the circumferential direction of the meshed tubular portion 12 being tubular; and the plurality of first intersecting points 123 are formed side by side in the circumferential direction of the meshed tubular portion 12 being tubular, and arranged in the plurality of intersecting regions 134, respectively. As a result, the wavily woven portion 13 can be woven along the circumferential direction, whereby the expansion force of the outer stent 11 in the radial direction can be further strengthened.

(3c) When the first intersecting point 123 of the meshed tubular portion 12 is configured so as to be arranged in the intersecting region 134 of the wavily woven portion 13, the third fiber 131 is arranged in the state of being hookable by one or more of the first fiber 121, the second fiber 122, and the fourth fiber 132, in relation to movement in a direction in which the overlapping portion of the third fiber 131 and the fourth fiber 132 shrinks in size; and the fourth fiber 132 is arranged in the state of being hookable by one or more of the first fiber 121, the second fiber 122, and the third fiber 131, in relation to movement in a direction in which the overlapping portion of the third fiber 131 and the fourth fiber 132 shrinks in size. As a result, any of these fibers is hooked by the third fiber 131 and the fourth fiber 132 of the wavily woven portion 13, whereby displacement of the first intersecting point 123 can be prevented.

(3d) The wavily woven portion 13 (third fiber 131 and fourth fiber 132) is formed of synthetic resin fiber having an expansion force higher than the meshed tubular portion 12 (first fiber 121 and second fiber 122). As a result, the meshed tubular portion 12 being tubular is formed of the first fiber 121 and the second fiber 122, and the third fiber 131 and fourth fiber 132 can expand the first fiber 121 and the second fiber 122 in the radial direction; therefore, the expansion force in the radial direction can be further enhanced.

According to the biodegradable stent 10 of the second embodiment described above, similar to the effects of (1a) of the first embodiment, the following effects (4a) can be achieved.

(4a) The biodegradable stent 10 is configured to include the inner stent 6 including the inner stent body 71 formed of synthetic resin fiber into a tubular structure having a mesh, and being deformable from the reduced diameter state to the expanded diameter state; and the outer stent 11 formed into a tubular structure having a mesh denser than the mesh of the inner stent body 71, arranged so as to cover the outer periphery of the inner stent body 71, and being deformable from the reduced diameter state to the expanded diameter state. Therefore, the inner stent body 71 formed with a sparse mesh is arranged inside the outer stent 11 formed with a dense mesh, whereby the pressing force of the inner stent body 71 from the inside of the outer stent 11 can reinforce the strength of the outer stent 11, and the strength of the biodegradable stent 10 in its entirety can be ensured. As a result, the gastrointestinal tract can be pressed in the state in which the strength of the biodegradable stent 10 in its entirety is ensured by the pressing force of the inner stent body 71 from the inside of the outer stent 11, whereby the biodegradable stent 10 can be prevented from moving while preventing stenosis. Therefore, the biodegradable stent 10, which can exert self-expandability, restorability, adherence to the gastrointestinal tract, and trackability to peristaltic movement, can be achieved.

<First Variation of Second Embodiment>

Figure 11:
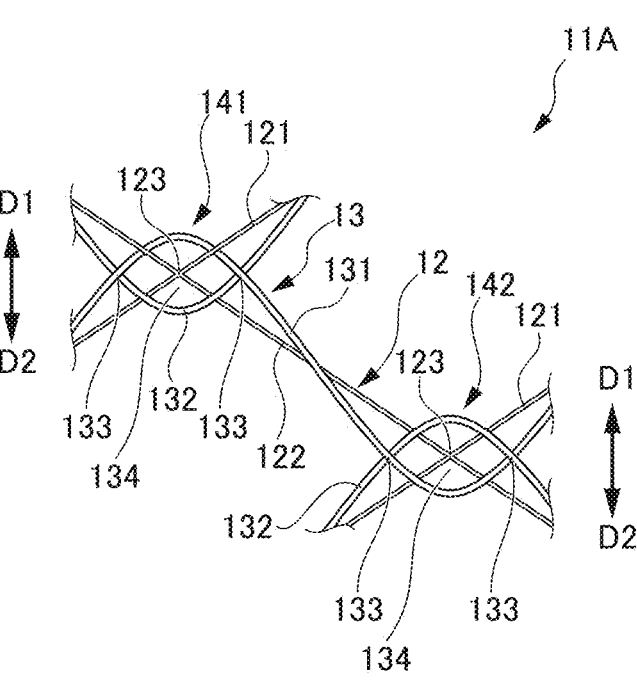
FIG. 11 is a view illustrating an outer stent according to a first variation of the second embodiment.

An outer stent 11A of a first variation of the second embodiment will be described. FIG. 11 is a view illustrating the outer stent 11A according to the first variation of the second embodiment. As illustrated in FIG. 11, the outer stent 11A of the first variation of the second embodiment is configured to include a first hooking portion 141 (left side in FIG. 11) and a second hooking portion 142 (right side in FIG. 11). The plurality of first hooking portions 141 and the plurality of second hooking portions 142 are spirally and alternately arranged in the circumferential direction in the outer stent 11A.

Since the configuration of the first hooking portion 141 illustrated in FIG. 11 is similar to that of the first hooking portion 141 described in the second embodiment, description thereof is omitted.

The configuration of the second hooking portion 142 will be described. As illustrated in FIG. 11, the first fiber 121 and the second fiber 122 of the meshed tubular portion 12 decussate at the first intersecting point 123 in the second hooking portion 142 as well, similar to the first hooking portion 141 of the second embodiment.

In the second hooking portion 142, the third fiber 131 is arranged frontside of the fourth fiber 132 at one of the two second intersecting points 133 (left side in FIG. 11) and arranged backside of the fourth fiber 132 at the other one of the second intersecting points 133 (right side in FIG. 11). As a result, the third fiber 131 and the fourth fiber 132 are arranged in the state of being mutually hookable, in relation to movement in a direction in which the mutually overlapping convex portion of the third fiber 131 and the fourth fiber 132 shrinks in size.

The first intersecting point 123 of the first fiber 121 and the second fiber 122 is arranged in the intersecting region 134 surrounded by the third fiber 131 and the fourth fiber 132 of the wavily woven portion 13.

As illustrated in FIG. 11, the first fiber 121 is arranged so as to be inclined and extending from the upper right side to the lower left side in the intersecting region 134, and passes the backside of the fourth fiber 132, intersects with the second fiber 122 at the first intersecting point 123, and passes the backside of the third fiber 131, from the upper right side to the lower left side. As illustrated in FIG. 11, the second fiber 122 is arranged so as to be inclined and extending from the upper left side to the lower right side in the intersecting region 134, passes the backside of the fourth fiber 132, intersects with the first fiber 121 at the first intersecting point 123, and passes the backside of the third fiber 131, from the upper left side to the lower right side. In other words, in the second hooking portion 142, the first fiber 121 and the second fiber 122 in their entirety are arranged backside of the third fiber 131 and the fourth fiber 132, whereby the third fiber 131 and the fourth fiber 132 in their entirety are arranged frontside of the first fiber 121 and the second fiber 122.

The first fiber 121, the second fiber 122, the third fiber 131, and the fourth fiber 132 are arranged as above, whereby, in the second hooking portion 142, the third fiber 131 and the fourth fiber 132 are arranged in the state of being mutually hookable, in relation to movement in a direction in which the mutually overlapping convex portion of the third fiber 131 and the fourth fiber 132 shrinks in size; the third fiber 131 and the fourth fiber 132 in their entirety are arranged frontside of the first fiber 121 and the second fiber 122; and the third fiber 131 and the fourth fiber 132 are arranged in the state of not being hookable by the first fiber 121 and the second fiber 122, in relation to movement of the third fiber 131 and the fourth fiber 132 in the first direction D1 or the second direction D2 direction.

According to the outer stent 11A of the first variation of the second embodiment described above, in addition to the effects (3a) to (3d) described above, the following effects can be achieved. (3e) The plurality of configurations are provided, in which the first intersecting point 123 of the meshed tubular portion 12 is arranged in the intersecting region 134 of the wavily woven portion 13; and the third fiber 131 and fourth fiber 132 are arranged in the state of being mutually hookable, in relation to movement in a direction in which the overlapping portion of the third fiber 131 and fourth fiber 132 shrinks in size, and also arranged in the state of not being hookable by the first fiber 121 and the second fiber 122 when the third fiber 131 and fourth fiber 132 move. As a result, the third fiber 131 and/or the fourth fiber 132 are/is arranged in the state of not being hookable by the first fiber 121 and the second fiber 122, whereby the length in the axial direction is unlikely to be restricted when the outer stent 11A is extended; therefore, loadability into a delivery system can be improved.

<Second Variation of Second Embodiment>

Figure 12:
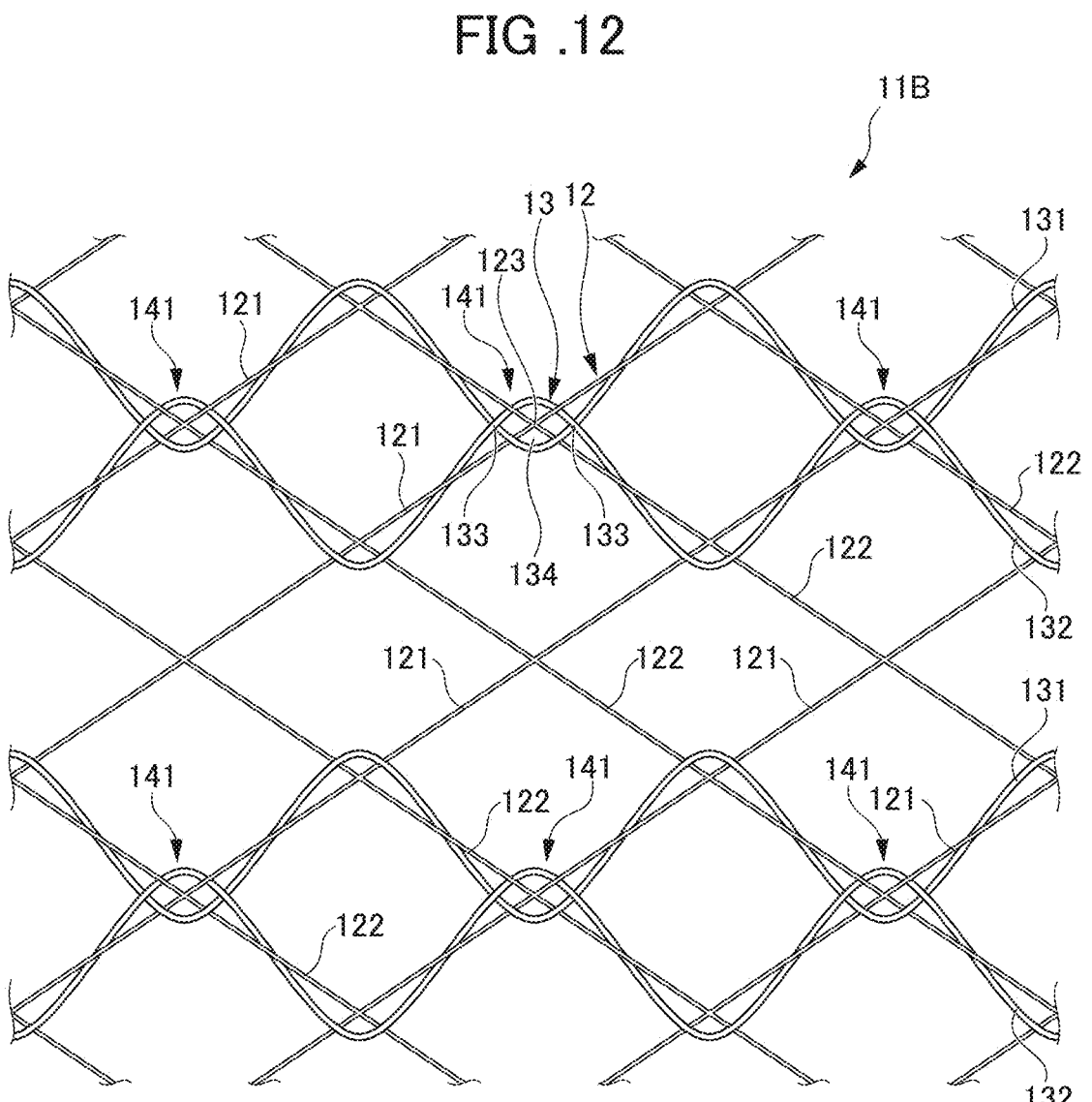
FIG. 12 is a view illustrating an outer stent according to a second variation of the second embodiment.

An outer stent 11B of a second variation of the second embodiment will be described. FIG. 12 is a view illustrating the outer stent 11B according to the second variation of the second embodiment. As compared with the outer stent 11 of the second embodiment, in the case of the outer stent 11B of the second variation of the second embodiment, the rows of the plurality of first hooking portions 141 arranged in the circumferential direction are arranged so as to be spaced one row apart from each other, instead of being packed in the axial direction of the outer stent 11A, in the wave-shaped wavily woven portion 13 (second woven component portion) woven into the meshed tubular portion 12 (first woven component portion).

As illustrated in FIG. 12, the wavily woven portion 13 is configured to include a row in which the plurality of first hooking portion 141 are arranged side by side in the circumferential direction, and a row without the first hooking portions 141, in the axial direction of the meshed tubular portion 12 having the plurality of first intersecting points 123. The first intersecting point 123 is arranged in the intersecting region 134 of the wavily woven portion 13 in the first hooking portion 141, in the row in which the plurality of first hooking portions 141 are arranged side by side in the circumferential direction. The plurality of first intersecting points 123 are arranged side by side in the circumferential direction, in the row without the first hooking portions 141.

According to the outer stent 11B of the second variation of the second embodiment described above, in addition to the effects (3a) to (3e) described above, the following effects can be achieved.

(3f) The rows of the plurality of first hooking portions 141 arranged in the circumferential direction are arranged so as to be spaced one row apart from each other in the axial direction. As a result, the rows without the first hooking portions 141 are provided, instead of packing the first hooking portions 141 in the axial direction of the outer stent 11B, whereby the length in the axial direction is unlikely to be restricted by the third fiber 131 and the fourth fiber 132 when the outer stent 11B is extended; therefore, loadability into a delivery system can be improved.

<Third Variation of Second Embodiment>

Figure 13:
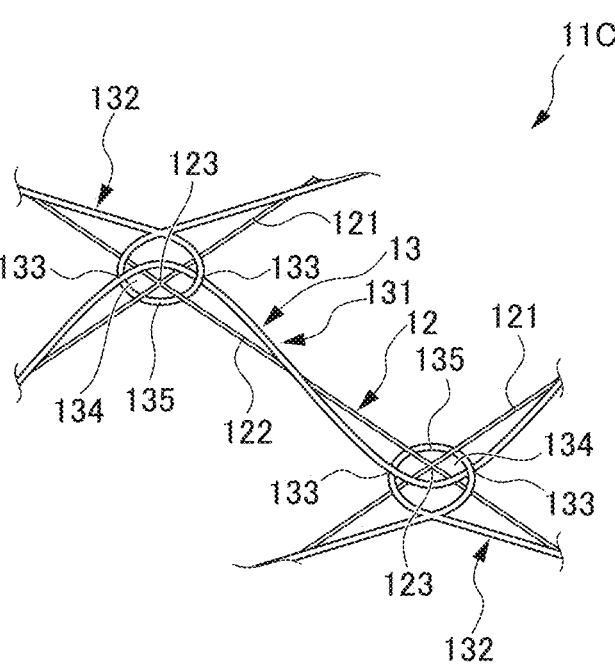
FIG. 13 is a view illustrating an outer stent according to a third variation of the second embodiment.

An outer stent 11C of the third variation of the second embodiment will be described. FIG. 13 is a view illustrating the outer stent 11C according to the third variation of the second embodiment.

As illustrated in FIG. 13, the outer stent 11C of the third variation of the second embodiment includes a plurality of loops 135 formed at the top of the peaks of the wave-shaped fourth fiber 132. The loop 135 is formed into a loop shape surrounding the first fiber 121, the second fiber 122, the third fiber 131, and the fourth fiber 132, in which the first intersecting point 123 of the meshed tubular portion 12 is arranged in the intersecting region 134 of the wavily woven portion 13.

The plurality of loops 135 may be consecutively provided at the top of the peaks of the wave-shaped fourth fiber 132, or may be intermittently provided at the top of the plurality of peaks of the wave-shaped fourth fiber 132. The loops 135 may not be configured to surround all of the first fiber 121, the second fiber 122, the third fiber 131, and the fourth fiber 132, or may be configured to surround only part of the first fiber 121, the second fiber 122, the third fiber 131, and the fourth fiber 132.

According to the outer stent 11C of the third variation of the second embodiment described above, in addition to the effects (3a) to (3f) described above, the following effects can be achieved.

(3g) The loops 135 are provided at the top of the peaks of the wave-shaped third fiber 131 and/or the wave-shaped fourth fiber 132. Here, for example, in the case without the loops 135 at the top of the peaks of the wavily woven portion 13, only an expansion force in the radial direction is applied to the wave-shaped third fiber 131 and the wave-shaped fourth fiber 132 of the wavily woven portion 13; therefore, it is difficult to control the diametrical size of the outer stent 11C. In contrast, in the present invention, the loops 135 can apply a contraction force in the radial direction; therefore, the diametrical size of the outer stent 11C can be controlled.

<Fourth Variation of Second Embodiment>

Figure 14:
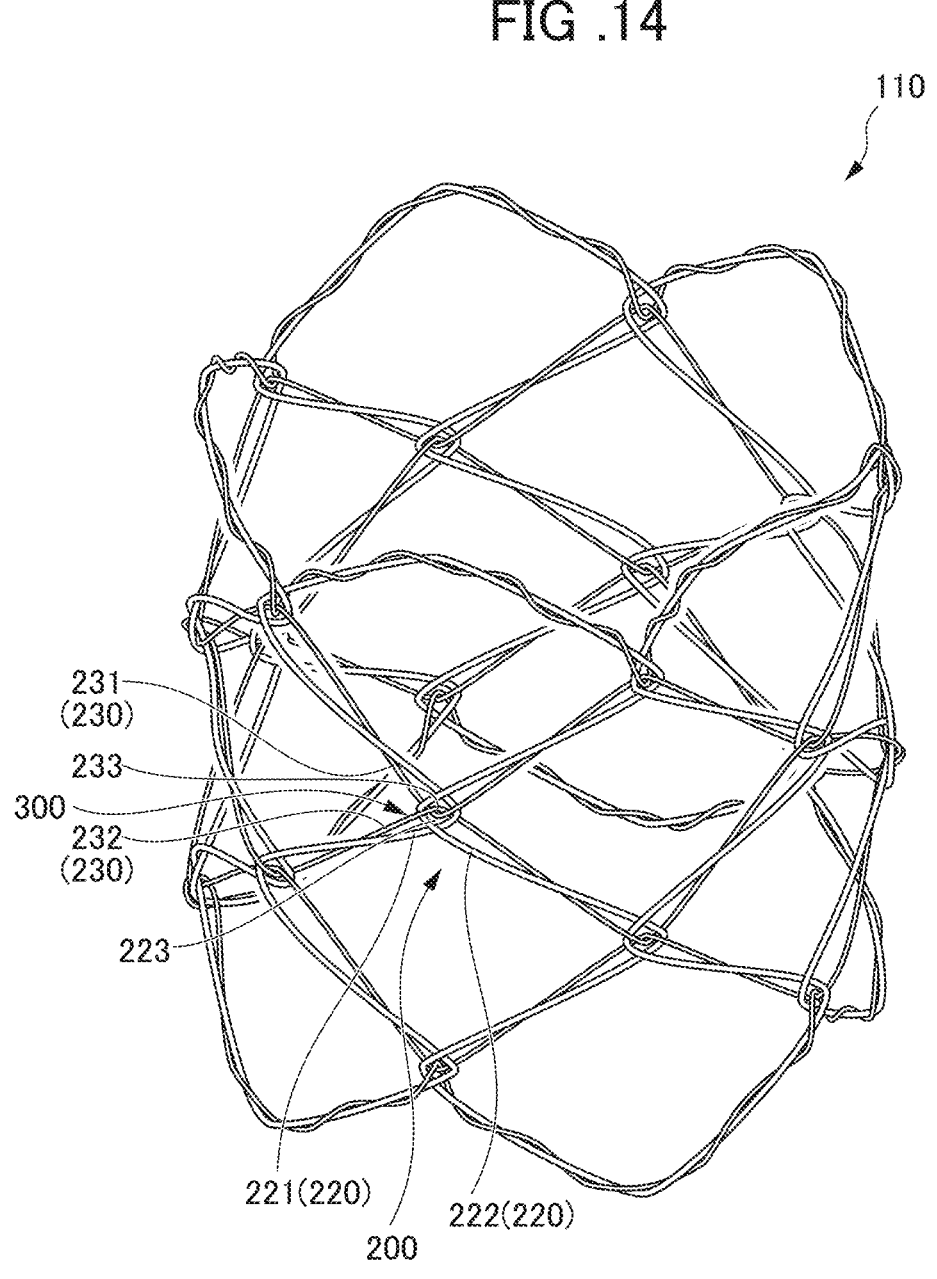
FIG. 14 is a perspective view illustrating a biodegradable stent according to a fourth variation of the second embodiment of the present invention.
Figure 15:
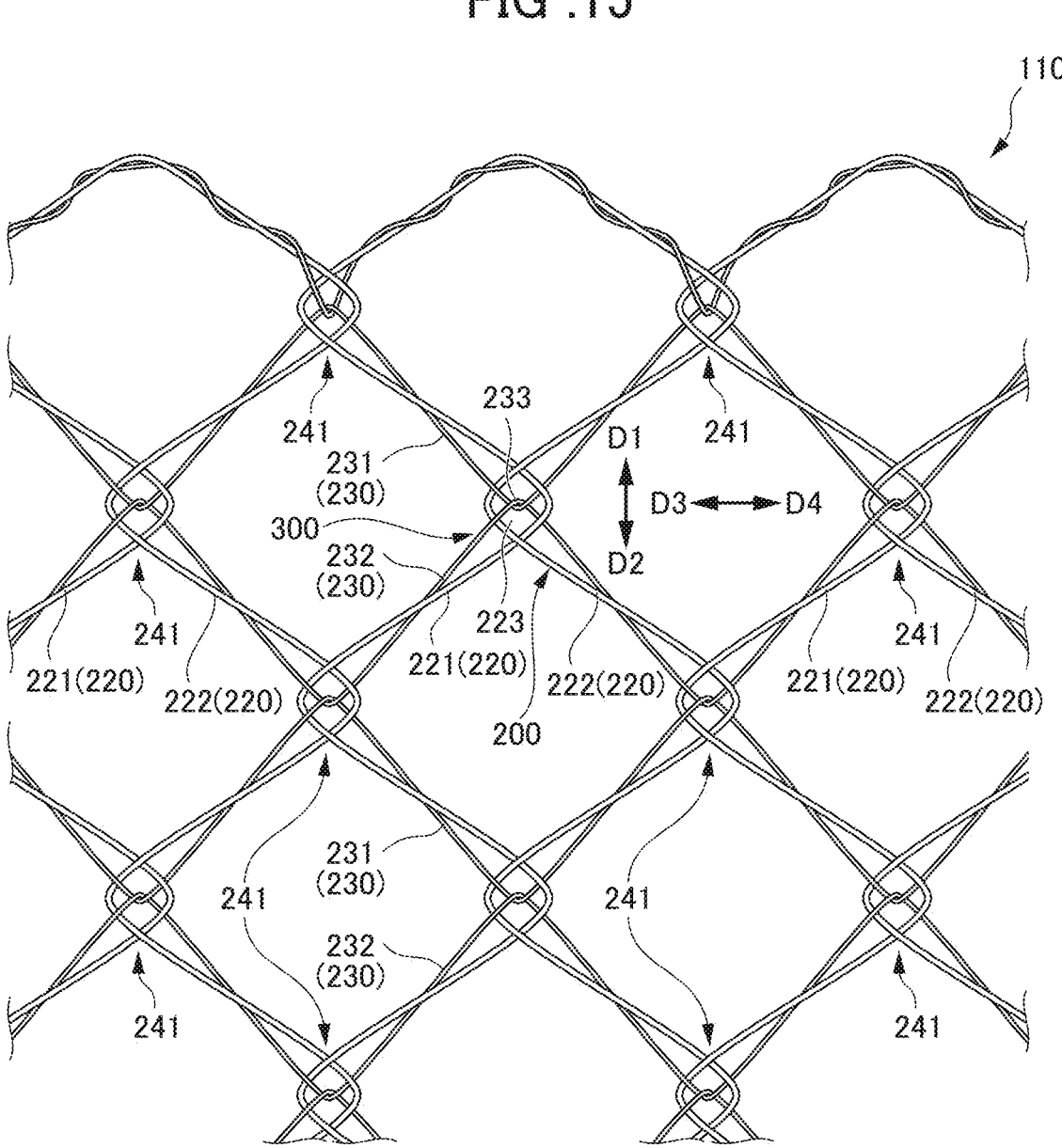
FIG. 15 is an enlarged view of the biodegradable stent illustrated in FIG. 14.

Referring to FIGS. 14 and 15, an outer stent 110 according to a fourth variation of the second embodiment will be described. FIG. 14 is a perspective view illustrating the outer stent 110 according to the fourth variation of the second embodiment of the present invention. FIG. 15 is an enlarged view of the outer stent 110 illustrated in FIG. 14. In the outer stent 110 illustrated in FIG. 15, one side in the axial direction is referred to as a first direction D1, and the other side in the axial direction is referred to as a second direction D2. In the outer stent 110, one side in the circumferential direction is referred to as a third direction D3 (left side of FIG. 15), and the other side in the circumferential direction is referred to as a fourth direction D4 (right side of FIG. 15).

As illustrated in FIGS. 14 and 15, the synthetic resin stent of the present embodiment is the outer stent 110 composed of biodegradable fiber, and includes a first bent woven portion 200 (first woven component portion) and a second bent woven portion 300 (second woven component portion) arranged so as to be woven in the first bent woven portion 200.

The first bent woven portion 200 is formed into a mesh, in which a plurality of fibers 220 repeatedly bent so as to extend in the axial direction are arranged in the circumferential direction and formed into a tubular structure. In the present embodiment, as illustrated in FIG. 15, the fiber 220 configuring the first bent woven portion 200 is configured with a plurality of first fibers 221 and a plurality of second fibers 222.

The plurality of first fibers 221 are formed of synthetic resin fiber repeatedly bent so as to be inclined at a predetermined angle with respect to the axial direction and extending in the axial direction. The plurality of first fibers 221 are repeatedly bent and extend in the axial direction so as to shuttle in a predetermined range of width in the circumferential direction of the first bent woven portion 200.

The plurality of second fibers 222 are arranged to include a portion intersecting with the plurality of first fibers 221, and formed of synthetic resin fiber repeatedly bent so as to shuttle and extending in the axial direction. The plurality of second fibers 222 are repeatedly bent and extend in the axial direction so as to shuttle in a predetermined range of width in the circumferential direction of the first bent woven portion 200.

In the present embodiment, the plurality of first fibers 221 and the plurality of second fibers 222 are composed of a single fiber, folding back at the upper and lower ends of the first bent woven portion 200 in the axial direction. The plurality of first fibers 221 and the plurality of second fibers 222 are part of a single fiber. In other words, the first fiber 221 and the second fiber 222 are alternately arranged in the circumferential direction of the first bent woven portion 200. The first bent woven portion 200 may be configured with a plurality of fibers.

More specifically, as illustrated in FIG. 15, the first fiber 221 and the second fiber 222 both include a plurality of bent portions including peaks convex toward the third direction D3 side and peaks convex toward the fourth direction D4 side. As viewed from the side, the first fiber 221 and the second fiber 222 are arranged to have bent portions overlapping with each other and intersect in the first intersecting region 223. The first fiber 221 and the second fiber 222 are formed such that the region surrounded by the first fiber 221 and the second fiber 222 is an opening having a substantially diamond shape in the first intersecting region 223.

In the first intersecting region 223, the first fiber 221 and the second fiber 222 may be arranged so as to overlap with each other as viewed from the side, and may be hooked by each other or may not be hooked by each other. In the present embodiment, the bent portions of the first fiber 221 and the second fiber 222 are hooked by each other in the upper end portion and the lower end portion of the outer stent 110 in the axial direction, and are not hooked by each other in portions excluding the upper end portion and the lower end portion of the outer stent 110 in the axial direction. The first intersecting regions 223 are arranged side by side in both the axial direction and the circumferential direction of the first bent woven portion 200.

The first intersecting region 223 is formed such that the region surrounded by the first fiber 221 and the second fiber 222 is an opening. However, the size of the opening of the first intersecting region 223 is not limited. In the first intersecting region 223, the first fiber 221 and the second fiber 222 may pull each other in the overlapping portion in a direction to shrink in size, so that the first fiber 221 and the second fiber 222 may be hooked by each other, whereby the region surrounded by the first 221 and the second fiber 222 may not be an opening.

The material of the first fiber 221 and the second fiber 222 is not limited in particular; however, a material having a high degree of rigidity is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of rigidity. In particular, for example, polylactic acid (PLA) or poly-L-lactic acid (PLLA) is preferably used as the material of the fiber composing the first fiber 221 and the second fiber 222. In the present embodiment, the first fibers 221 and the second fiber 222 are formed from polylactic acid (PLA), for example.

In the case of using biodegradable fiber as the fiber 220, the diameter thereof is preferably 0.1 mm to 0.4 mm. When the diameter of the biodegradable fiber 220 is less than 0.1 mm, the strength of the outer stent 110 tends to decrease. When the diameter of the biodegradable fiber 20 exceeds 0.4 mm, the diameter in the reduced diameter state increases, so that it tends to be difficult to load the outer stent 110 into a fine tubular member such as a delivery system. The upper limit of the diameter of the biodegradable fiber 20 is further preferably 0.3 mm, from a perspective of loading into a delivery system having a small inner diameter. The lower limit of the diameter of the biodegradable fiber 220 is more preferably 0.2 mm, from a perspective of maintaining high strength. In the present embodiment, biodegradable fiber having a diameter of 0.2 mm and biodegradable fiber having a diameter of 0.3 mm are used as the fibers 220.

As illustrated in FIGS. 14 and 15, the second bent woven portion 300 is arranged so as to be woven into the first bent woven portion 200, in which a plurality of circularly configured fibers 230 repeatedly bent so as to extend in the circumferential direction are arranged side by side in the axial direction. In the present embodiment, as illustrated in FIG. 15, the fiber 230 configuring the second bent woven portion 300 is configured with a plurality of third fibers 231 and a plurality of fourth fibers 232.

The plurality of third fibers 231 are formed of synthetic resin fiber repeatedly bent so as to be inclined at a predetermined angle with respect to the axial direction and extending in the circumferential direction. The plurality of third fibers 231 are repeatedly bent and extend in the circumferential direction so as to shuttle in a predetermined range of width in the axial direction of the second bent woven portion 300.

The plurality of fourth fibers 232 are arranged to include a portion intersecting with the plurality of third fibers 231, and formed of synthetic resin fiber repeatedly bent so as to extend in the circumferential direction. The plurality of fourth fibers 232 are repeatedly bent and extend in the circumferential direction so as to shuttle in a predetermined range of width in the axial direction of the second bent woven portion 300.

More specifically, the third fiber 231 and the fourth fiber 232 both include a plurality of bent portions including peaks convex toward the first direction D1 side and peaks convex toward the second direction D2 side. As viewed from the side, the third fiber 231 and the fourth fiber 232 are arranged to have bent portions overlapping with each other and intersect in the second intersecting region 233. In the second intersecting region 233, the third fiber 231 and the fourth fiber 232 may be arranged so as to overlap with each other as viewed from the side, and may be hooked by each other or may not be hooked by each other. In the present embodiment, the bent portions of the third fiber 231 and the fourth fiber 232 are hooked by each other in the second intersecting region 233, and the region surrounded by the third fiber 231 and the fourth fiber 232 is not an opening. The second intersecting regions 233 are arranged side by side in the axial direction and the circumferential direction of the second bent woven portion 300.

The bent portions of the third fiber 231 and the fourth fiber 232 are hooked by each other, and the region surrounded by the third 231 and the fourth fiber 232 is not an opening in the second intersecting region 233, which is not limited, however. The region surrounded by the third 231 and the fourth fiber 232 may be an opening in the second intersecting region 233, and the size of the opening in the second intersecting region 233 is not limited.

Of the plurality of third fibers 231 and the plurality of fourth fibers 232, the third fiber 231 or the fourth fiber 232 arranged at the upper end or the lower end of the outer stent 110 is arranged so as to be wound around the first fiber 221 or the second fiber 222 of the first bent woven portion 200.

The material of the synthetic resin fiber configuring the third fiber 231 and the fourth fiber 232 is not limited in particular; however, a material having a high degree of restorability is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of restorability. For example, polydioxanone (PDO) is preferably used as the material of the third fiber 231 and the fourth fiber 232.

In the case of using biodegradable fiber as the fiber 230, the diameter thereof is preferably 0.1 mm to 0.4 mm. In the present embodiment, the biodegradable fiber having a diameter of 0.15 mm to 0.22 mm is used as the fiber 230.

The first intersecting region 223 of the first bent woven portion 200 and the second intersecting region 233 of the second bent woven portion 300 are arranged so as to be at least partially overlapping with each other, as the outer stent 110 is viewed from the side. The at least partially overlapping portion of the second intersecting region 233 of the second bent woven portion 300 and the second intersecting region 233 of the first bent woven portion 200 configures a hooking portion 241. The outer stent 110 of the present embodiment includes a plurality of hooking portions 241, in which a row of the hooking portions 241 arranged in the circumferential direction is formed throughout the axial direction.

The configuration of the hooking portion 241 will be described. FIG. 15 is a view, in which the radial direction of the tubular outer stent of 110 in FIG. 14 is rearranged along the direction perpendicular to the paper (direction penetrating the paper) of FIG. 15. Therefore, the inside of the outer stent 110 in the radial direction is the backside in the vertical direction of the paper of FIG. 15; and the outer side of the outer stent 110 in the radial direction is the frontside in the vertical direction of the paper of FIG. 15. Some parts of the upper and lower ends of the outer stent 110 in the axial direction are woven to prevent the fibers from coming apart. Here, the hooking portion 241 in the present embodiment will be described for the portions excluding the upper and lower ends of the outer stent 110 in the axial direction.

As illustrated in FIG. 15, the second intersecting region 233 of the third fiber 231 and the fourth fiber 232 is arranged in the first intersecting region 223 surrounded by the first fiber 221 and the second fiber 222, in the hooking portion 241.

The first fiber 221 and the second fiber 222 of the first bent woven portion 200 are arranged to include an opening in the first intersecting region 223 in the hooking portion 241, in which a bent portion convex toward the third-direction D3 side and a bent portion convex toward the fourth-direction D4 side overlap with each other.

The third fiber 231 and the fourth fiber 232 of the second bent woven portion 300 are arranged in the state in which a bent portion convex toward the first direction D1 side and a bent portion convex toward the second direction D2 side are hooked by each other, in the second intersecting region 233 in the hooking portion 241.

As illustrated in FIG. 15, the bent portion convex toward the third direction D3 side in the first fiber 221 and the second fiber 222 of the first bent woven portion 200 passes the backside of the third fiber 231 and the fourth fiber 232 on the apex side of the convex portion (third direction D3 side), and passes the frontside of the third fiber 231 and the fourth fiber 232 on the opening side of the convex portion (fourth direction D4 side), in the hooking portion 241. The bent portion convex toward the fourth direction D4 side in the first fiber 221 and the second fiber 222 passes the frontside of the third fiber 231 and the fourth fiber 232 on the apex side of the convex portion (fourth direction D4 side), and passes the frontside of the third fiber 231 and the fourth fiber 232 on the opening side of the convex portion (third direction D3 side). The bent portion convex toward the third direction D3 side in the first fiber 221 and the second fiber 222 passes the frontside of the bent portion convex toward the fourth direction D4 side.

The first fiber 221, the second fiber 222, the third fiber 231, and the fourth fiber 232 are arranged as above, whereby, in the hooking portion 241, the first fiber 221 is arranged in the state of being hookable by the third fiber 231 and the fourth fiber 232, in relation to movement in a direction in which the mutually overlapping convex portion of the first fiber 221 and the second fiber 222 shrinks in size; and the second fiber 222 is arranged in the state of being hookable by the third fiber 231 and the fourth fiber 232, in relation to movement in a direction in which the mutually overlapping convex portion of the first fiber 221 and the second fiber 222 shrinks in size.

The outer stent 110 as described above may be manufactured by forming the second bent woven portion 300 and then forming the first bent woven portion 200, or conversely, by forming the first bent woven portion 200 and then forming the second bent woven portion 300.

The outer stent 110 configured as described above is formed into a tubular structure with the first fiber 221 and the second fiber 222 repeatedly bent so as to be inclined with respect to the axial direction and extending in the axial direction in the first bent woven portion 200, whereby the shape of the stent is maintained in the tubular structure. The second bent woven portion 300 is woven into the first bent woven portion 200, the second bent woven portion 300 (third fiber 231 and fourth fiber 232) is formed of synthetic resin fiber having a higher expansion force than the first bent woven portion 200 (first fiber 221 and second fiber 222), and the bent portion thereof has a property of returning to a straight line. Therefore, the second bent woven portion 300 is woven and repeatedly bent so as to circle the first bent woven portion 200 in the circumferential direction, whereby the second 300 can apply a force to increase the diameter of the outer stent 110, and can enhance the expansion force. Thus, the expansion force of the outer stent 110 in the radial direction can be strengthened to achieve self-expandability. Adherence to the wall of the gastrointestinal tract can be increased, and trackability to gastrointestinal motility can be achieved.

According to the outer stent 110 of the fourth variation of the second embodiment described above, the following effects can be achieved.

(4a) The outer stent 110 is configured to include the tubular first bent woven portion 200 composed of one or more fibers formed into a mesh, and the second bent woven portion 300 composed of one or more fibers annularly arranged so as to be woven into the first bent woven portion 200; the first bent woven portion 200 is configured to include the plurality of first fibers 221 repeatedly bent so as to be inclined at a predetermined angle with respect to the axial direction and extending in the axial direction, the plurality of second fiber 222 repeatedly bent so as to be inclined at a predetermined angle with respect to the axial direction and extending in the axial direction and arranged to include a portion intersecting with the first fiber 221, and the plurality of first intersecting regions 223 configured by intersections of the plurality of first fibers 221 and the plurality of second fibers 222; the second bent woven portion 300 is configured to include the plurality of third fibers 231 repeatedly bent so as to be inclined at a predetermined angle with respect to the axial direction and extending in the circumferential direction; the plurality of fourth fiber 232 repeatedly bent so as to be inclined at a predetermined angle with respect to the axial direction and extending in the axial direction and arranged to include a portion intersecting with the third fiber 231, and the plurality of second intersecting regions 233 configured by intersections of the plurality of third fibers 231 and the plurality of fourth fibers 232; and the first intersecting region 223 and the second intersecting region 233 are arranged so as to be at least partially overlapping with each other.

As a result, the first fiber 221 and the second fiber 222 repeatedly bent so as to be inclined at a predetermined angle with respect to the axial direction and extending in the axial direction maintains the first bent woven portion 200 in the tubular structure, whereby the tubular structure of the outer stent 110 is maintained. The second bent woven portion 300 is woven into the first bent woven portion 200, and the first intersecting region 223 of the first bent woven portion 200 and the second intersecting region 233 of the second bent woven portion 300 are arranged to at least partially overlap with each other, whereby the second bent woven portion 300 can apply a force to increase the diameter, and can enhance the expansion force in the radial direction. Thus, the expansion force of the outer stent 110 in the radial direction can be strengthened to achieve self-expandability. Adherence to the wall of the gastrointestinal tract can be increased, and trackability to gastrointestinal motility can be achieved. Therefore, the stent can ensure loadability into a fine tubular member such as a delivery system, in which migration of the stent is unlikely to occur after placement at the affected site of the natural tracts.

(4b) In the configuration in which the first intersecting region 223 of the first bent woven portion 200 and the second intersecting region 233 of the second bent woven portion 300 are arranged to overlap each other, the first fiber 221 is arranged in the state of being hookable by one or more of the third fiber 231 and the fourth fiber 232, in relation to movement in a direction in which the overlapping portion of the first fiber 221 and the second fiber 222 shrinks in size; and the second fiber 222 is arranged in the state of being hookable by one or more of the third fiber 231 and the fourth fiber 232, in relation to movement in a direction in which the overlapping portion of the first fiber 221 and the second fiber 222 shrinks in size. As a result, the first fiber 221 and the second fiber 222 of the first bent woven portion 200 are hooked by any one of the third fiber 231 and the fourth fiber 232, whereby displacement of the first intersecting region 223 and the second intersecting region 233 can be prevented.

A manufacture example and an example of the biodegradable stent of the first to third variations of the second embodiment will be briefly described. In the present manufacture example, the outer stent 11A of the first variation of the second embodiment (see FIG. 11) and the outer stent 11B of the second variation of the second embodiment (see FIG. 12) are manufactured by braiding six PLA fibers (three fibers having a fiber diameter of 0.2 mm, and three fibers having a fiber diameter of 0.3 mm), and using PDO fiber having a fiber diameter of 0.15 mm to 0.22 mm to manufacture a wave shape. The outer stent 11C of the third variation of the second embodiment (see FIG. 13) is manufactured by braiding six PLA fibers (having a diameter of 0.2 mm) and using PDO fiber to manufacture a wave shape with a fiber diameter of 0.30 mm to 0.349 mm, and a loop shape with a fiber diameter of 0.15 mm to 0.22 mm. The outer stents 11A, 11B and 11C are formed by weaving and winding the PLA fiber around the PDO fiber having a wave shape, whereby the shape of the stents is unlikely to collapse.

The outer stents 11A, 11B and 11C are manufactured under the conditions described above, whereby a stent loadable into a delivery system for the small intestine ($\varphi$ 2.8 mm) can be achieved. In the case of use in other gastrointestinal tracts, the diameter of the delivery system increases and the fiber diameter can increase as well, whereby a stent having further higher strength can be expected to be manufactured. The fiber diameter as well as the stent diameter and length may be arbitrary.

The outer stents 11A and 11C thus prepared were used to conduct the following experiment. A tool manufactured in-house to simulate peristaltic movement was used to conduct a migration test on the stents. The tool for use in the present test simulates peristaltic movement, in which the stent was placed inside a tube mimicking the intestinal tract, and the tube was squeezed 10 times with a tool having a hole-diameter of 10 mm, assuming that the intestinal tract shrinks to φ 10 mm due to peristaltic movement.

In an intestinal tract model in which the diameter of the intestinal tract expands to φ 17 mm and shrinks to φ 10 mm during peristaltic movement, the outer stent 11A of the second embodiment (stent having a length of 55 mm) moved by 35 mm. In an intestinal tract model in which the diameter of the intestinal tract expands to φ 12 mm and shrinks to φ 10 mm during peristaltic movement, the outer stent 11C of the third variation of the second embodiment (stent having a length of 36 mm) moved by 10 mm. In the same intestinal tract models, a metallic stent (stent having a length of 110 mm) moved by 40 mm, suggesting that the outer stents 11A and 11C of the first and third variations of the second embodiment have trackability to the intestinal tract.

The preferred embodiments of the synthetic resin stent of the present invention have been described above; however, the present invention is not limited to the embodiments and can be modified as appropriate.

For example, the biodegradable stent composed of biodegradable fiber has been used as a synthetic resin stent in the embodiments, which are not limited. In other words, nonbiodegradable synthetic resin fiber may be used to compose a stent.

The plurality of first hooking portions 141 are provided to the outer stent 11 in its entirety, in the second embodiment. The first hooking portions 141 and the second hooking portions 142 are alternately provided, in the third variation of the second embodiment. The plurality of first hooking portions 141 are arranged side by side in the circumferential direction, in the second variation of the second embodiment. However, the present invention is not limited to the embodiments, and the first hooking portions 141 and/or the second hooking portions 142 may not be provided to the biodegradable stent in its entirety, or may be provided to part of the biodegradable stent.

In the second embodiment, the loop 135 is provided at the top of the peaks of the wave-shaped fourth fiber 132, which is not limited, and may be provided at the top of the peaks at the wave-shaped third fiber 131.

The preferred embodiments of the synthetic resin stent and the stent delivery system of the present invention have been described above; however, the present invention is not limited to the embodiments and can be modified as appropriate.

For example, the biodegradable stent composed of biodegradable fiber is used as a synthetic resin stent in the embodiments, which are not limited. In other words, nonbiodegradable synthetic resin fiber may be used to compose a stent.

The biodegradable stent 1 is configured by combining the inner stent 2 and the outer stent 5 in the first embodiment, and the biodegradable stent 10 is configured by combining the inner stent 6 and the outer stent 11 in the second embodiment; however, the present invention is not limited thereto. The biodegradable stent may be configured by combining the inner stent 2 of the first embodiment and the outer stent 11 of the second embodiment, or may be configured by combining the inner stent 6 of the second embodiment and the outer stent 5 of the first embodiment.

EXPLANATION OF REFERENCE NUMERALS 1, 10: biodegradable stent (synthetic resin stent)
2: inner stent (first stent)
3: inner stent body (first stent body)
4: end flare portion (end enlarged diameter portion)
5: outer stent (second stent)
6: inner stent (first stent)
11, 11a, 11b, 11c, 110: outer stent (second stent)
32: tubular connecting portion (connecting portion)
311: polygonal annular portion
200: first bent woven portion (first woven component portion)
300: second bent woven portion (second woven component portion)
221: first fiber
222: second fiber
223: first intersecting region
231: third fiber
232: fourth fiber
233: second intersecting region
241: hooking portion

The invention claimed is:

1. A synthetic resin stent, comprising:
a first stent including a first stent body formed of synthetic resin fiber into a tubular structure having a mesh, the first stent being deformable from a reduced diameter state to an expanded diameter state; and
a second stent formed into a tubular structure having a mesh denser than the mesh of the first stent body, the second stent arranged so as to cover an outer periphery of the first stent body, and being deformable from the reduced diameter state to the expanded diameter state,
wherein the first stent body is formed by connecting a plurality of polygonal annular portions side by side in a longitudinal direction of the first stent, in a state in which the plurality of polygonal annular portions formed of synthetic resin fiber into a polygonal annular shape as viewed in the longitudinal direction are bent or curved so as to be convex in the longitudinal direction,
the plurality of polygonal annular portions each include a pair of bent portions that are bent so as to be convex toward one side in the longitudinal direction, and a pair of bent portions that are bent so as to be convex toward one other side in the longitudinal direction,
the plurality of polygonal annular portions are configured by connecting the plurality of polygonal annular portions side by side in the longitudinal direction in such a manner that, in a state in which bent portions of adjacent polygonal annular portions are arranged to face each other, the bent portions of the adjacent polygonal annular portions that face each other are connected by a corresponding one of tubular connecting portions, and
a pair of the adjacent polygonal annular portions is connected with each other such that mutual convex portions made of synthetic resin fiber of the pair of the adjacent polygonal annular portions is connected with each other with a corresponding one of the tubular connecting portions that connect the bent portions that are bent so as to be convex toward one side in the longitudinal direction and the bent portions that are bent so as to be convex toward one other side in the longitudinal direction.

2. The synthetic resin stent according to claim 1, wherein the first stent further includes an end enlarged diameter portion connected to at least one end of the first stent body in the longitudinal direction, the end enlarged diameter portion being larger in diameter than the first stent body.

3. The synthetic resin stent according to claim 2, wherein the end enlarged diameter portion is formed of synthetic resin fiber, the synthetic resin fiber of the end enlarged diameter portion has a diameter smaller than the synthetic resin fiber of the plurality of polygonal annular portions of the first stent body, the end enlarged diameter portion is configured into a polygonal annular structure, wherein the polygonal annular structure of the end enlarged diameter portion has more peaks and valleys than the plurality of polygonal annular portions of the first stent body.

4. The synthetic resin stent according to claim 1, wherein the first stent is a stent including an end flare portion arranged at an end in an axial direction, the first stent being formed of wires, a plurality of peaks composed of tip corners protruding outward in the axial direction are consecutively arranged in a circumferential direction, whereby the end flare portion is formed into an annular shape as viewed in the axial direction, an angle formed by two sides of each of the peaks is 80° or less in a state in which the stent is placed inside the gastrointestinal tract, and the number of the plurality of peaks is three to eleven.

5. The synthetic resin stent according to claim 4, wherein the two sides composing each of the peaks are composed of two sides of an end grid arranged at an end in the axial direction.

6. The synthetic resin stent according to claim 5, wherein the first stent includes a plurality of grids arranged side by side in the axial direction, and the end grid is arranged at an end of the plurality of grids.

7. The synthetic resin stent according to claim 4, wherein one side length of one of the two sides composing each of the peaks is 16 mm to 22 mm.

8. The synthetic resin stent according to claim 4, wherein adjacent ones of the peaks of the end flare portion are fixed at an intersection to the most end-side in the axial direction.

9. The synthetic resin stent according to claim 1, wherein the second stent is a synthetic resin stent including a first woven component portion being tubular and composed of a plurality of fibers woven into a mesh, and a second woven component portion composed of a plurality of fibers arranged so as to be woven into the first woven component portion and configured into an annular shape, the first woven component portion includes a plurality of first fibers extending so as to be inclined at a predetermined angle with respect to the axial direction, a plurality of second fibers extending so as to intersect with the first fibers, and a plurality of first intersecting points configured with intersections of the plurality of first fibers and the plurality of second fibers, the second woven component portion includes a plurality of wave-shaped third fibers arranged so as to be spaced apart in the axial direction, and a plurality of wave-shaped fourth fibers arranged so as to be spaced apart in the axial direction, and at least one first intersecting point of the plurality of first intersecting points is arranged in intersecting regions surrounded by the third fibers and the fourth fibers.

10. The synthetic resin stent according to claim 9, wherein the plurality of intersecting regions are formed side by side in the circumferential direction of the first woven component portion, and the plurality of first intersecting points are arranged side by side in the circumferential direction of the first woven component portion and arranged in the plurality of intersecting regions, respectively.

11. The synthetic resin stent according to claim 9, wherein in a configuration in which the first intersecting points are arranged in the intersecting regions, respectively, the third fibers are arranged in a state of being hookable by one or more of the first fibers, the second fibers and the fourth fibers, in relation to movement in a direction in which an overlapping portion of the third fibers and the fourth fibers shrinks in size, and the fourth fibers are arranged in a state of being hookable by one or more of the first fibers, the second fibers and the third fibers, in relation to movement in a direction in which the overlapping portion of the third fibers and the fourth fibers shrinks in size.

12. The synthetic resin stent according to claim 11, further comprising a plurality of configurations in which the first intersecting point is arranged in the intersecting region, wherein the synthetic resin stent is configured to partly include a configuration, in which the third fibers and the fourth fibers are arranged in a state of being mutually hookable, in relation to movement in a direction in which the overlapping portion of the third fibers and the fourth fibers shrinks in size, and arranged in a state of not being hookable by the first fibers and the second fibers when the third fibers and the fourth fibers move.

13. The synthetic resin stent according to claim 9, wherein a loop having a loop shape is formed at the top of the peaks of the wave-shaped third fibers and/or the wave-shaped fourth fibers, the loop arranged so as to surround any one or more of the first fibers, the second fibers, the third fibers and the fourth fibers.

14. The synthetic resin stent according to claim 9, wherein the second woven component portion is formed of synthetic resin fiber having an expansion force higher than the first woven component portion.

15. The synthetic resin stent according to claim 1, wherein the second stent is a synthetic resin stent including a first woven component portion being tubular and composed of one more fibers configured into a mesh, and a second woven component portion arranged so as to be woven into the first woven component portion and composed of one or more fibers configured into an annular shape, the first woven component portion includes a plurality of first fibers repeatedly bent so as to be inclined at a predetermined angle with respect to the axial direction and extending in the axial direction, a plurality of second fibers arranged to include a portion intersecting with the first fibers and repeatedly bent so as to be inclined at a predetermined angle with respect to the axial direction and extending in the axial direction, and a plurality of first intersecting regions configured with intersections of the plurality of first fibers and the plurality of second fibers, the second woven component portion includes a plurality of third fibers repeatedly bent so as to be inclined at a predetermined angle with respect to the axial direction and extending in the circumferential direction, a plurality of fourth fibers arranged to include a portion intersecting with the third fibers and repeatedly bent so as to be inclined at a predetermined angle with respect to the axial direction and extending in the axial direction, and a plurality of second intersecting regions configured with intersections of the plurality of third fibers and the plurality of fourth fibers, and the first intersecting regions and the second intersecting regions are arranged to at least partly overlap with each other.

16. The synthetic resin stent according to claim 15, wherein in a configuration in which the first intersecting region is arranged to overlap with the second intersecting region, the first fibers are arranged in a state of being hookable by one or more of the third fibers and the fourth fibers, in relation to movement in a direction in which an overlapping portion of the first fibers and the second fibers shrinks in size, and the second fibers are arranged in a state of being hookable by one or more of the third fibers and the fourth fibers, in relation to movement in a direction in which an overlapping portion of the first fibers and the second fibers shrinks in size.

17. A stent delivery system comprising:

the synthetic resin stent of claim 1;

an outer tube that can interiorly load the first stent and the second stent, wherein the second stent and the first stent are arranged side by side in this order from the distal end side; and a pushing member that is arranged inside the outer tube and can extrude the second stent and the first stent in this order from the distal end side of the outer tube.

\* \* \* \* \*